US011399779B2

(12) United States Patent
Wilson et al.

(10) Patent No.: US 11,399,779 B2
(45) Date of Patent: Aug. 2, 2022

(54) SYSTEM-INDEPENDENT QUANTITATIVE PERFUSION IMAGING

(71) Applicant: Case Western Reserve University, Cleveland, OH (US)

(72) Inventors: David L. Wilson, Cleveland Heights, OH (US); Brendan L. Eck, Cleveland Heights, OH (US); Jacob Levi, University Heights, OH (US); Hao Wu, Cleveland Heights, OH (US); Rachid Fahmi, Knoxville, TN (US)

(73) Assignee: Case Western Reserve University, Cleveland, OH (US)

( * ) Notice: Subject to any disclaimer, the term of this patent is extended or adjusted under 35 U.S.C. 154(b) by 104 days.

(21) Appl. No.: 16/356,296

(22) Filed: Mar. 18, 2019

(65) Prior Publication Data

US 2019/0350538 A1 Nov. 21, 2019

Related U.S. Application Data

(60) Provisional application No. 62/672,129, filed on May 16, 2018.

(51) Int. Cl.
*A61B 6/03* (2006.01)
*A61B 5/026* (2006.01)
(Continued)

(52) U.S. Cl.
CPC .............. *A61B 6/03* (2013.01); *A61B 5/0261* (2013.01); *A61B 5/6886* (2013.01);
(Continued)

(58) Field of Classification Search
CPC ....... A61B 6/03; A61B 5/0261; A61B 5/6886; G06F 9/3004; G06T 11/003–008; G06T 5/00–005; G06T 7/0012–0016
See application file for complete search history.

(56) References Cited

U.S. PATENT DOCUMENTS 7,940,974 B2 * 5/2011 Skinner ..................... G06T 7/12
382/131
10,789,738 B2 * 9/2020 Pan ........................ G06T 11/005
(Continued)

OTHER PUBLICATIONS

Pimrak et al. "A novel Approach to reduce partial scan artifacts in Cardiac multidetector row CT" RSNA 2008 (Year: 2008).*
(Continued)

*Primary Examiner* — Sean T Motsinger
(74) *Attorney, Agent, or Firm* — Eschweiler & Potashnik, LLC

(57) ABSTRACT

Embodiments discussed herein facilitate system-independent quantitative perfusion measurements. One example embodiment is a method, comprising: accessing 4D (Four Dimensional) perfusion imaging data of a tissue, where the 4D perfusion imaging data comprises a plurality of 3D (Three Dimensional) stacks of perfusion imaging data over time; performing at least one of artifact reduction or post-processing on the 4D perfusion image data to generate processed 4D perfusion image data; computing one or more quantitative perfusion parameters for the tissue based at least in part on the processed 4D perfusion image data; and outputting a visual representation of the one or more quantitative perfusion parameters.

20 Claims, 10 Drawing Sheets

(51) Int. Cl.
  *A61B 5/00*  (2006.01)
  *G06F 9/30*  (2018.01)
  *G06T 5/00*  (2006.01)
  *G06T 7/00*  (2017.01)
(52) U.S. Cl.
  CPC ............ *G06F 9/3004* (2013.01); *G06T 5/001* (2013.01); *G06T 7/0012* (2013.01); *G06T 2207/10076* (2013.01); *G06T 2207/10088* (2013.01)

(56) References Cited

U.S. PATENT DOCUMENTS

| | | | | |
|---|---|---|---|---|
| 2003/0211036 | A1* | 11/2003 | Degani | G06T 7/0012 424/1.11 |
| 2006/0159223 | A1* | 7/2006 | Wu | A61B 6/032 378/18 |
| 2007/0127789 | A1* | 6/2007 | Hoppel | A61B 6/5247 382/128 |
| 2009/0003666 | A1* | 1/2009 | Wu | G06T 7/0012 382/128 |
| 2009/0041179 | A1* | 2/2009 | Zellerhoff | A61B 6/4441 378/4 |
| 2011/0103664 | A1* | 5/2011 | Kovalski | G06T 7/33 382/131 |
| 2011/0150309 | A1* | 6/2011 | Barfett | G06T 7/11 382/131 |
| 2012/0045109 | A1* | 2/2012 | Proksa | A61B 6/504 382/131 |
| 2012/0051614 | A1* | 3/2012 | Olszewski | G06T 7/0002 382/128 |
| 2012/0121145 | A1* | 5/2012 | Funabasama | A61B 6/5217 382/128 |
| 2012/0243761 | A1* | 9/2012 | Senzig | A61B 6/504 382/131 |
| 2013/0266201 | A1* | 10/2013 | Pautot | A61B 5/0263 382/131 |
| 2014/0163403 | A1* | 6/2014 | Lenox | A61B 5/7235 600/504 |
| 2014/0192950 | A1* | 7/2014 | Pelc | A61B 6/4035 378/4 |
| 2014/0257094 | A1* | 9/2014 | Meetz | A61B 6/461 600/425 |
| 2014/0294141 | A1* | 10/2014 | Hsieh | G02B 5/201 378/19 |
| 2016/0048955 | A1* | 2/2016 | Carmi | G06T 7/11 382/131 |
| 2016/0148379 | A1* | 5/2016 | Ditt | G06T 11/008 382/131 |
| 2016/0279084 | A1* | 9/2016 | Haaga | A61K 31/05 |
| 2017/0039735 | A1* | 2/2017 | Can | G01N 33/24 |
| 2018/0174314 | A1* | 6/2018 | Bippus | G06T 11/006 |
| 2018/0279943 | A1* | 10/2018 | Budman | G06T 7/0014 |
| 2019/0057506 | A1* | 2/2019 | Long | G06T 7/0016 |
| 2019/0274542 | A1* | 9/2019 | Imamura | A61B 3/102 |
| 2019/0350538 | A1* | 11/2019 | Wilson | A61B 6/507 |

OTHER PUBLICATIONS

Wu et al. "SLIC robust processing for fast rubst CT myocardial blood flow quantification" Proceedings vol. 10578, Medical Imaging 2018: Biomedical Applications in Molecular, Structural, and Functional Imaging; 105781U (2018) Mar. 12, 2018 (Year: 2018).*
Kyriakou et al. "Emerical beam hardening correction (EBCH) for CT" Med Phys Oct. 2010;. (Year: 2010).*

* cited by examiner

SYSTEM-INDEPENDENT QUANTITATIVE PERFUSION IMAGING

CROSS REFERENCE TO RELATED APPLICATIONS

This application claims the benefit of U.S. Provisional Patent Application No. 62/672,129 filed May 16, 2018, entitled "SYSTEM-INDEPENDENT QUANTITATIVE CARDIAC CT PERFUSION", the contents of which are herein incorporated by reference in their entirety.

BACKGROUND

Cardiac perfusion measurements (e.g., via Computed Tomography (CT), etc.) can be useful for evaluation of cardiovascular disease. However, for CT systems, beam hardening creates tell-tale artifacts in the enhancing myocardium, which negatively affect flow measurements. One existing solution is to use specialized, expensive energy-sensitive CT systems which can generate nearly beam-hardening free images. However, such systems are not readily available.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
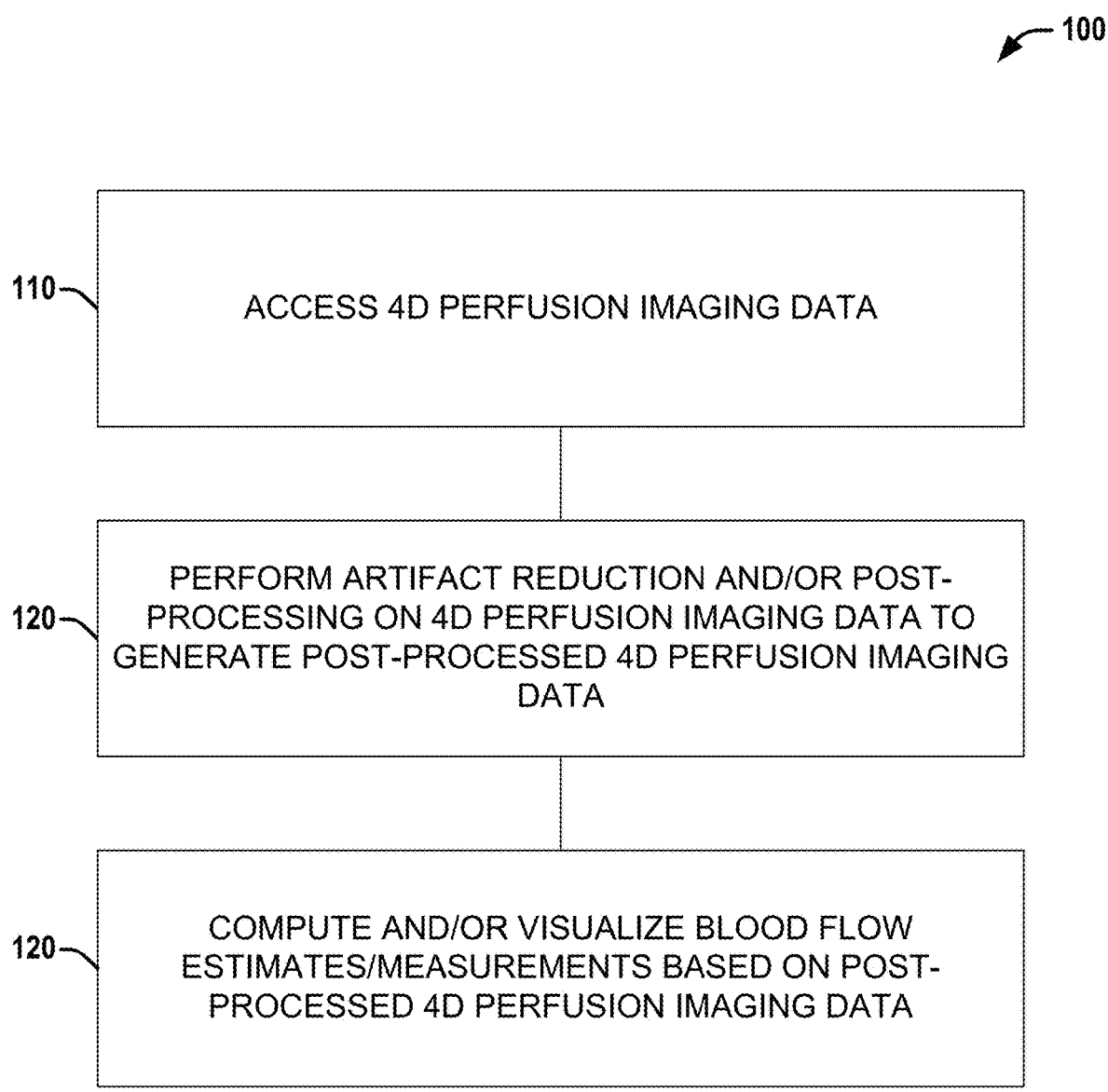
FIG. 1 illustrates a flow diagram of a first example method/set of operations that can be performed by one or more processors to obtain system-independent perfusion measurements, according to various aspects discussed herein.

Various embodiments discussed herein can facilitate quantitative cardiac computed tomography (CT) perfusion measurements that can be performed on any perfusion-ready commercial CT system, creating an important tool for evaluation of cardiovascular disease. Various embodiments discussed herein can address multiple issues related to the limited usage of CT for perfusion measurements. First, beam hardening creates tell-tale artifacts in the enhancing myocardium, which negatively affect flow measurements. As noted above, one existing solution is to use specialized, expensive, energy-sensitive CT systems which can generate nearly beam-hardening free images. However, such systems are not readily available. Accordingly, various embodiments employing CT technology can employ automatic beam hardening correction (ABHC) techniques discussed herein which can be used on any CT scanner. Second, x-ray dose to patients is an issue in dynamic CT imaging, and tissue dosing can be an issue in other imaging techniques as well (e.g., SAR (specific absorption rate) issues in ultrasound, MRI, etc.). Various embodiments can employ a super-voxel technique discussed herein that can aggregate originally acquired voxels. This technique can effectively reduce noise and can enable high quality blood flow estimates in the presence of low x-ray-dose imaging, or similar lower energy imaging with other medical imaging systems (e.g., MRI (Magnetic Resonance Imaging), ultrasound, PET (Positron-Emission Tomography), SPECT (Single-Photon Emission Computed Tomography), etc.). Third, various embodiments can employ flow estimation approaches discussed herein that can give much more accurate and precise measurements than existing methods.

Various embodiments associated with CT systems can be important as Cardiac CT perfusion (CCTP) can provide an important non-invasive measurement for the diagnosis of coronary artery disease. With such embodiments, cardiologists can be able to identify functional flow deficits in coronary artery territories. When myocardial blood flow (MBF) is coupled with evaluation of coronary anatomy from computed tomography angiography (CTA), it can provide important information on the physiologic significance of a stenosis, providing a gateway exam for percutaneous invasive coronary angiography and potential intervention (e.g., stenting). In addition, if flow is low and no stenosis is present, it will suggest microvascular disease, an ailment of great concern. By providing quantitative flow measurements, there is the potential to create non-invasive diagnostic criteria for micro-vascular disease in a single CT examination. There are significant market drivers. Cardiovascular disease remains the number one cause of death, with a recent, alarming increase, likely due to obesity and diabetes. A combined CTA/CCTP assessment with could reduce the 60% of unnecessary elective invasive coronary angiography studies, giving significant cost savings. There is increasing attention to coronary microvascular disease, with prevalence estimates from 20% to 50% for persons affected by chest pain, especially in women. CT compares favorably to all other non-invasive cardiovascular imaging techniques (SPECT, PET, and MRI). CT is available in many settings, including emergency departments, and provides both MBF and reliable coronary anatomy, not available in any other single modality. Additionally, CT has excellent resolution enabling detection of endocardial perfusion deficit, thought to be an early disease indicator and impossible to detect with SPECT, and is cheaper than MRI or PET. With the inclusion of MBF, as provided via various embodiments discussed herein, CT can provide an excellent opportunity to disrupt the diagnostic pathway leading to percutaneous intervention, a pathway now dominated by myocardial SPECT, which has questionable accuracy and gives no anatomical information.

Various embodiments related to CCTP can provide an improved gateway examination that can reduce unnecessary invasive coronary angiography, thereby reducing costs, patient discomfort, patient risk, and possibly unnecessary interventional therapies.

Techniques described herein can be used for embodiments employing any of a variety of CT scanners, including basic CT systems where a spectrum of x-ray energies is used; energy sensitive CT such as fast kVp switching, spectral detector CT, and dual source CT, as well as emerging photon counting CT systems. In various embodiments, modifications can be employed when different scanners are used, as will be apparent to a person of ordinary skill in the art in view of the disclosure herein.

In various embodiments, techniques discussed herein can facilitate system-independent quantitative perfusion imaging. For the purposes of illustration of techniques discussed herein, various embodiments related to system-independent CT cardiac perfusion are discussed, although in other embodiments, perfusion imaging techniques discussed herein can be employed in connection with other imaging techniques and/or other tissues.

Embodiments discussed herein can employ one or more of four different sets of techniques discussed herein. A first set of techniques relates to processing pipeline(s) that can be employed for computing and/or visualizing blood flow from imaging data. A second set of techniques relate to Automatic Beam Hardening Correction (ABHC) techniques employable in various embodiments. A third set of techniques comprise techniques for robust estimation of flow and derived flow measurements. A fourth set of techniques relate to estimation of flow confidence intervals for blood flow measurements. Various embodiments can employ at least one of the first set of techniques, the second set of techniques, the third set of techniques, or the fourth set of techniques, each of which is described in greater detail below.

Although various specific examples are provided in the context of cardiac CT perfusion, various embodiments can be employed in other use cases. As an example, each of the first through fourth set of techniques are applicable to CT perfusion assessments in other tissues (e.g., brain, tumor, etc.). Additionally, each of the first set of techniques, the third set of techniques, and the fourth set of techniques are applicable to perfusion assessments with other imaging modalities (e.g., MRI, ultrasound, PET, SPECT, etc.).

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of a first example method/set of operations 100 that can be performed by one or more processors to obtain system-independent perfusion measurements, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing a set of 4D perfusion imaging data. The set of 4D perfusion imaging data can comprise a time ordered set of 3D perfusion images (e.g., DICOM images) of a given tissue obtained via a medical imaging system (e.g., CT, PET, MRI, ultrasound, SPECT, etc.). The given tissue can vary based on the embodiment and/or use case, and can be, for example, cardiac, brain, tumor, etc. The imaging data can be obtained via a system and/or apparatus implementing the set of operations 100, or can be obtained from a separate medical imaging system 100. Additionally, the imaging data can be accessed contemporaneously with or at any point prior to performing the set of operations 100. Although techniques discussed herein can be applied independently of the type of imaging system that generated the 4D perfusion imaging data, in some scenarios, certain operations or acts can be omitted or included based on the type of imaging system employed.

The set of operations 100 can further comprise, at 120, performing artifact reduction and/or post-processing on the accessed set of 4D perfusion imaging data to generate a set of processed 4D perfusion imaging data. The specific operations involved in artifact reduction and/or post-processing can vary between embodiments, and can comprise one or more of the artifact reduction and/or post-processing operations described in greater detail below.

The set of operations 100 can further comprise, at 130, computing and/or visualizing one or more quantitative perfusion measurements and/or confidence estimates of quantitative perfusion measurements based on the set of processed 4D perfusion imaging data. The one or more quantitative perfusion measurements can comprise blood flow (e.g., myocardial blood flow in cardiac embodiments, etc.), flow rate to fill the intravascular volume (FRIV, discussed in greater detail below), flow ratio(s) (e.g., stress blood flow divided by rest blood flow, etc.), and/or confidence estimates associated with any quantitative perfusion measurements. Computed perfusion measurement(s) and/or confidence estimates can be output in a variety of manners, including by outputting graphical and/or numerical representations of the perfusion measurements and/or confidence estimates, such as via color coded maps of blood flow and/or other measurements (e.g., ratios, etc., polar plots, multi-segment displays, etc.

Figure 2:
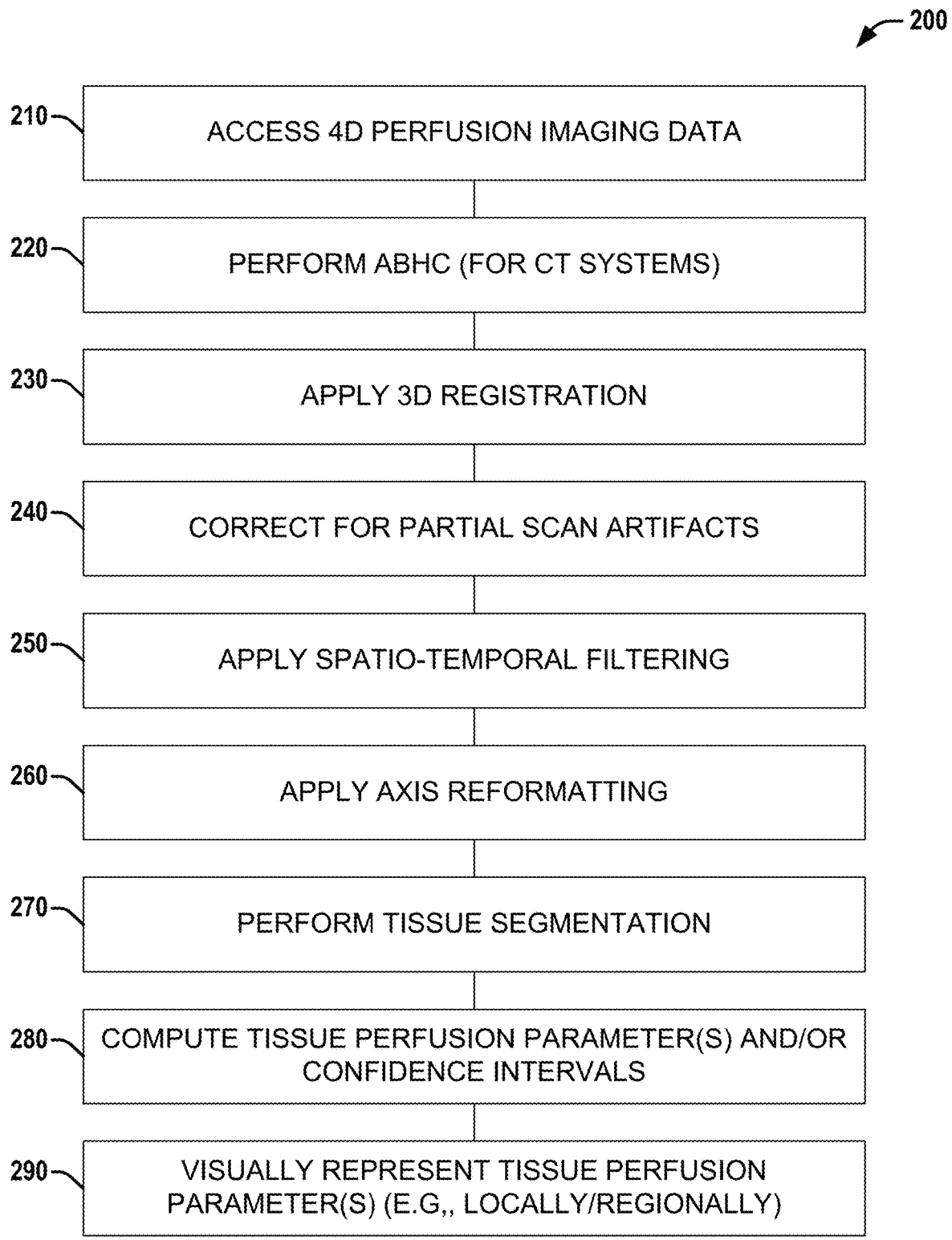
FIG. 2 illustrates a flow diagram of a second example set of operations that can be performed by one or more processors to obtain system-independent perfusion measurements, according to various aspects discussed herein.

Referring to FIG. 2, illustrated is a flow diagram of a second example set of operations 200 that can be performed by one or more processors to obtain system-independent perfusion measurements, according to various aspects discussed herein. The set of operations 200 is similar to the set of operations 100, but can comprise additional details and elements.

Operations 200 can comprise, at 210, accessing a set of 4D perfusion imaging data, which can be similar to operation 110 and/or as described herein.

Operations 200 can further comprise one or more of the specific artifact reduction and/or post-processing operations to generate a set of processed 4D perfusion imaging data, such as example operations 220-270. In general, operations 220-270 can each provide for more accurate perfusion measurements, at the cost of increased processing and computation. Thus, in various embodiments, one or more of operations 220-270 can be omitted, or each of operations 220-270 can be performed.

Operations 200 can optionally comprise (e.g., for CT systems), at 220, correcting for beam hardening artifacts in CT imaging data (e.g., via Automated Beam Hardening Correction techniques discussed herein). Automated Beam Hardening Correction can be applied based on any of a variety of models as discussed herein. In some embodiments, multiple corrections can be calculated, and a best correction can be applied (e.g., via machine learning).

Operations 200 can also optionally comprise, at 230, correcting for motion artifacts in the imaging data via 3D registration of image frames (e.g., via a non-rigid image transformation model, etc.). Although patient motion will always create some motion artifacts, in some use cases (e.g., cardiac), 3D registration will provide even greater benefits, due to natural motion of the tissue.

Operations 200 can also optionally comprise, at 240, correcting for shading artifacts introduced by partial scan acquisitions and reconstructions, based on a virtual full scan image that can be generated by averaging the full dynamic image sequence of 4D image data.

Operations 200 can also optionally comprise, at 250, reducing the effect of fluctuations arising from partial scan artifacts by applying spatio-temporal filtering, such as an edge-preserving 3D spatio-temporal filter discussed in greater detail below.

Operations 200 can also optionally comprise, at 260, reformatting the image data along a particular axis, which can be based on the tissue. For example, axial slices forming cardiac imaging data can be reformatted into cardiac short axis slices. As another example, axial slices forming tumor imaging can be reformatted parallel to a long axis of the tumor.

Operations 200 can also optionally comprise, at 270, segmenting one or more regions of the tissue. Segmentation can be performed in a semi-automated manner based on user-defined points placed along one or more boundaries associated with the regions.

Operations 200 can also comprise, at 280, one or more tissue perfusion parameters can be computed based on the set of processed 4D perfusion imaging data (e.g., blood flow, one or more flow ratios, flow rate to fill the intravascular volume as discussed herein, etc.), based at least in part on one or more models and/or algorithms discussed herein. Tissue perfusion parameter(s), in various embodiments, can also comprise regional estimates based on combinations of voxels and/or super-voxels. Additionally, confidence intervals can optionally be estimated for at least one of the one or more tissue parameters.

Operations 200 can also optionally comprise, at 290, visually representing the one or more tissue perfusion parameters and/or estimated confidence interval(s) by generating graphical and/or numerical representations based on the processed 4D perfusion imaging data and computed perfusion parameters. Visual representation can be performed according to any of a variety of techniques discussed herein, for example, 2D and/or 3D visualizations (e.g., which can be color-coded based on perfusion parameter(s), polar plots, 17-segment displays, color-coded maps, etc. In various embodiments, regional quantifications computed at operation 280 also can be visually represented, as described in greater detail below.

Example Use Case: System-Independent CCTP (Cardiac CT Perfusion)

The following discussion provides example embodiments in connection with an example use case involving cardiac CT (Computed Tomography) perfusion imaging.

Processing Pipeline

In the example use case, the image processing pipeline takes 4D (Four Dimensional) CCTP (Cardiac Computed Tomography Perfusion) data as inputs (e.g., 3D stacks of DICOM (Digital Imaging and Communications in Medicine) images over time), applies artifact reduction and/or post-processing steps, computes quantitative perfusion maps, and can visualize results. In the specific use case of CCTP, example data can be EKG (Electrocardiogram) gated with image volumes acquired once per heartbeat. However, other acquisition arrangements are possible.

Figure 3:
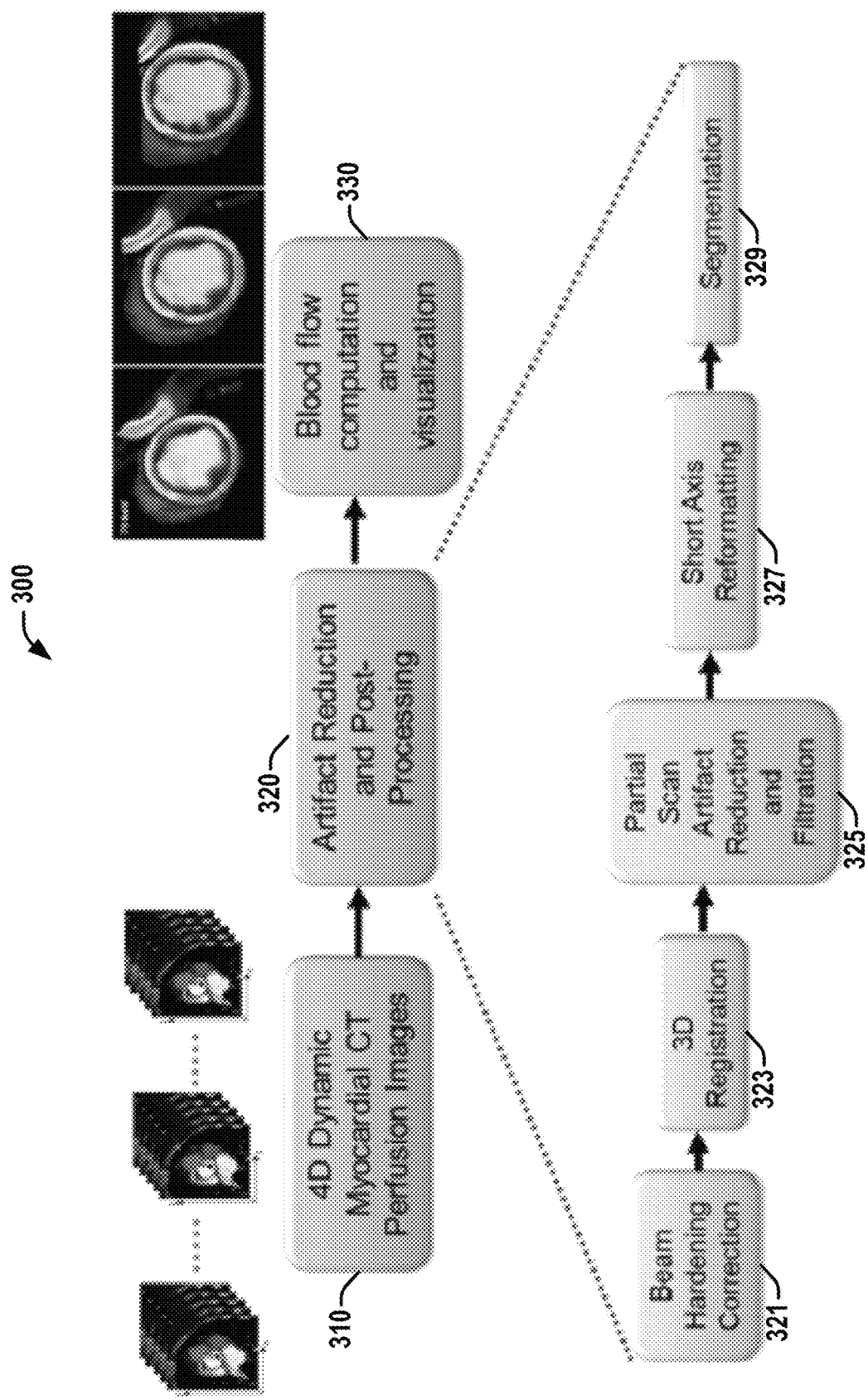
FIG. 3 illustrates a diagram of an example system-independent MPI (Myocardial Perfusion Imaging)-CT (Computed Tomography) processing pipeline, according to various embodiments discussed herein.

Referring to FIG. 3, illustrated is a diagram showing an example system-independent MPI (Myocardial Perfusion Imaging)-CT (Computed Tomography) processing pipeline of method 300, according to various embodiments discussed herein. In example processing pipeline of method 300, a set of CT images are input into the pipeline at 310 and several artifact reduction and post-processing acts are performed at 320 (with individual acts shown at 321-329). After artifact correction and post-processing, blood flow computation is performed at 330. The output of the pipeline is a set of quantitative perfusion maps. As shown in the example processing pipeline of method 300, artifact reduction and post-processing 320 comprises performing beam hardening correction (e.g., via automated beam hardening correction (ABHC) techniques discussed herein) on the images 321, 3D registration of the images at 323, performing partial scan artifact reduction and filtration on the images at 325, reformatting the image data to the short axis at 327, and image segmentation at 329. In various other embodiments, one or more of the acts shown in FIG. 3 can be omitted, and additional acts not shown in FIG. 3 can be included, as discussed in greater detail herein.

In example processing pipeline of method 300, Automated Beam Hardening Correction (ABHC) is applied at 321. Beam hardening correction can be applied to reduce beam hardening artifacts that can otherwise be interpreted as perfusion defects and that could interfere with accurate and precise quantitative perfusion analysis. The image-based ABHC algorithm (e.g., according to aspects discussed herein) can automatically determine correction parameters for a beam hardening correction model and apply those parameters to reduce artifacts in the image. In other embodiments, ABHC can be omitted, such as when non-CT imaging is employed, or if the CT system employed is an energy-sensitive CT system that generates imaging without significant beam hardening.

In example processing pipeline of method 300, 3D registration is applied at 323. The pipeline applies 3D registration to improve data quality by minimizing motion between image frames, particularly at the edges between the myocardium and ventricle blood pools or the myocardium and lung. The algorithm employed for 3D registration in various aspects uses a non-rigid image transformation model to achieve high-quality registration. One example spatial transformation method employable is bicubic splines, but other transformation models can be used in various embodiments. In one embodiment, image volumes at each time point are registered to the image volume at peak left ventricle (LV) cavity enhancement using a gray-scale similarity measure. This time was found to provide strong contrast between the LV cavity, RV (Right Ventricle) cavity, and myocardium. By registering to the same time point, the likelihood of "drift" during registration is reduced when compared to a sequential registration of adjacent image frames through time. Although 3D registration is employed in processing pipeline of method 300, in other embodiments (e.g., related to non-cardiac perfusion), 3D registration can be omitted, or can be included to account for other motion (e.g., patient motion, etc.).

In example processing pipeline of method 300, partial scan artifact reduction and/or filtration can be applied at 325.

In some embodiments, at 325, example processing pipeline of method 300 can apply an optional correction for partial scan acquisitions and reconstructions (e.g., 180 degree+fan angle) which are known to introduce shading artifacts. To address this, the algorithm determines the correction by generating a virtual full scan image by averaging the full dynamic image sequence, referred to herein as "FS" for full scan, and a corresponding partial scan by averaging partial scan images, referred to herein as "PS," acquired at the same acquisition angle as the current image, referred to herein as "I." The difference between FS and PS is the artifact correction. The corrected image, referred to herein as "Ic," is generated by Ic=I+FS−PS. In various embodiments, other techniques can be applied for artifact reduction.

Additionally, at 325, example processing pipeline of method 300 can apply spatio-temporal bilateral filtering to the images (in other embodiments, filtering can be omitted or other types of filtering can be employed). In example processing pipeline of method 300, an edge-preserving 3D spatio-temporal filter is applied at 325 to reduce the effect of fluctuations introduced by partial scan artifacts. The filter is applied to the 4D data in two different steps. First, for any given temporal position, 3D non-linear diffusion filtration is performed in the spatial domain. Second, the filter then operates on adjacent temporal positions.

In example processing pipeline of method 300, short axis reformatting is applied at 327. At 327, axial slices forming the 3D geometry are reformatted into cardiac short axis slices which are readily interpreted by physicians. Short axis images are generated to span the coverage of the heart. Typically, six 10-mm thick contiguous slices are generated (in various embodiments, the number and thickness of contiguous slices can vary, e.g., depending on the size of the tissue of interest). In various other embodiments, axis formatting can be omitted, or a different axis can be employed for reformatting (e.g., an axis parallel to a long axis of a tumor for tumor imaging data, etc.).

In example processing pipeline of method 300, segmentation is applied at 329. In the segmentation of example pipeline 300, the myocardium is segmented for myocardial blood flow computation, with segmentation performed on short axis slices. The segmentation can be performed via software, hardware, or a combination thereof, and can be semi-automated with user-defined points placed along the endocardial/LV cavity boundary and the epicardial/lung boundary, wherein the segmentation software (etc.) can then generate smooth contours fitted to the points. In other use cases, segmentation can be omitted, or can be performed in a similar manner with other tissue to separate along relevant boundaries.

In example processing pipeline of method 300, blood flow computation can be performed at 330. In a cardiac use case such as processing pipeline of method 300, myocardial blood flow, and optionally other relevant quantitative perfusion parameters, are computed using a robust physiologic model as discussed herein (in other use cases, other blood flow and/or additional perfusion parameters can be computed). Before blood flow computation, super-voxel clustering can be optionally performed, which can reduce noise, improve the quality of resultant flow maps, and greatly accelerate computation times. For blood flow computation, a user can defines the location and size of the ROI (Region of Interest) from which to obtain the arterial input function, usually placed in the LV cavity. Outputs from blood flow computation are the perfusion images for the CT volume and/or sub-volume(s).

In example processing pipeline of method 300, MBF (Myocardial Blood Flow) and regional quantification also can be performed at 330. In a cardiac use case such as processing pipeline of method 300, once MBF is estimated for voxels or super-voxels, visualization and quantification methods are applied. One technique employed by various embodiments is to map color-coded MBFs onto a physiologic 2D image to show a MBF map, such as the MBF map shown in FIG. 8, discussed below. Any number of regional MBF assessments can be performed by combining results from multiple voxels or super-voxels. Additionally, MBF over a flow deficit region can be estimated. A flow ratio can be obtained by measuring MBF in a flow deficit region and dividing by a reference tissue region. Additionally or alternatively to 2D slice visualizations, 3D visualizations of results can optionally be created. Techniques employable by various embodiments comprise polar plots and/or 17-segment displays as popularized for perfusion SPECT and PET imaging. Another such technique is 3D color-coded rendering of MBF. In the case of a rest-stress acquisition, a ratio map of stress MBF divided by rest MBF can be created, giving a myocardial perfusion reserve which is an indicator of coronary artery disease and microvascular disease.

Other embodiments of CT perfusion imaging are possible. Example processing pipeline of method 300 is designed to process images captured from an EKG gated, 8-cm longitudinal coverage, variable slice thickness, flying focal spot, multi-detector iCT CT scanner from Philips Healthcare with partial scan (240 degree) acquisitions. Many other CT systems are applicable, including but not limited to energy sensitive systems, 3D cone beam systems, C-arm system configurations, and large field of view scanners. In many cases, these alternative systems involve addition or detraction of pipeline elements. For example, in the case of energy-sensitive imaging, beam hardening correction can be replaced with a material decomposition algorithm or virtual keV reconstruction algorithm. As another example, if 360 degree acquisitions are obtained, partial scan corrections can be omitted.

Automatic Beam Hardening Correction

Automatic beam hardening correction (ABHC) can be employed in various CT-related embodiments, which can use an iterative approach to minimize a cost function and find optimal parameters for correcting beam hardening artifacts in a CT image. ABHC can be based on the empirical beam hardening correction (EBHC) algorithm (or, in various embodiments, some other parametric, image-based BH correction algorithm). The below discussion of the ABHC approach is preceded by a discussion of EBHC.

Empirical Beam Hardening Correction:

The following is a derivation of empirical beam hardening correction. A CT projection along ray L is given by equation (1):

$$q(L) = -\ln \int dE \Omega(L,E) e^{-\int_0^\infty dr\, \mu(E,r)} \quad (1)$$

where $\Omega(L,E)$ is the normalized spectrum along ray L. In the case of a single-material BH correction, the composition of equation (2) can be assumed:

$$\mu(E,r) = f_0(r)\psi_0(E) \quad (2)$$

where $\psi_0(E) = \mu_{en}\rho(E)$ is the mass-energy absorption coefficient which is the energy dependence of the material (e.g., water) and $f_0(r) = \rho(r)$ is the density at point r. Water pre-correction that is done on every CT scanner reconstructs $f_0(r)$ and equation (1) becomes equations (3):

$$q = -\ln \int dE \Omega(E) e^{P_0 \psi_0(E)} \quad (3)$$

$$P_0 = \int_0^\infty dr f_0(r)$$

The projection q is what is obtained from the scanner, which is a water corrected image that might suffer from BH (Beam Hardening) due to other HAMs (Highly Attenuated Materials). $P_0$ is the water image projection. For two materials, equation (2) becomes equations (4):

$$\mu(r,E) = f_1(r)\psi_1(E) + f_2(r)\psi_2(E) = \quad (4)$$
$$(f_1(r) + f_2(r))\psi_1(E) + f_2(r)(\psi_2(E) - \psi_1(E)) =$$
$$\hat{f}_1(r)\psi_1(E) + f_2(r)\hat{\psi}_2(E)$$

and equations (3) become equations (5):

$$q = -\ln \int dE \Omega(E) e^{-\hat{P}_1 \psi_1(E) - P_2 \hat{\psi}_2(E)} \quad (5)$$

$$\hat{P}_1 = \int_0^\infty \hat{f}_1(r) dr = \int_0^\infty (f_1(r) + f_2(r)) dr$$

Combining equations (3) and (5) gives equations (6):

$$\int dE \Omega(E) e^{P_0 \psi_0(E)} = \int dE \Omega(E) e^{-\hat{P}_1 \psi_1(E) - P_2 \hat{\psi}_2(E)} \quad (6)$$

Note that the LHS (Left Hand Side) is the projection data obtained from the scanner. Ideally, ABHC would present a BH artifact free image where $\hat{f}_1(r) = f_1(r) + f_2(r)$ and $\psi_1(E_0) = \psi_2(E_0) = 1$ (in various embodiments, images may have reduced BH artifacts, but may not be entirely BH artifact free). Using a series expansion for $\hat{P}_1$ (the corrected projection), equations (7) can be obtained:

$$\hat{P}_1(P_0, P_2) = \quad (7)$$
$$\sum_{i,j} c_{ij} P_0^i P_2^j = c_{10} P_0 + c_{01} P_2 + c_{11} P_0 P_2 + c_{20} P_0^2 + c_{02} P_2^2 + O(3+)$$

In order to determine the value of some of these parameters, a case with no HAMs in the image (i.e., $P_2 = 0$ and $P_1 = P_0$) can be checked. In that case, equation (8) applies:

$$c_{10} = 1 \text{ and } c_{10} = 0 \; \forall i \neq 1 \quad (8)$$

The final result is given by equation (9):

$$\hat{P}_1(P_0, P_2) = P_0 + c_{01} P_2 + c_{11} P_0 P_2 + c_{02} P_2^2 + O(3+) \quad (9)$$

Due to the linearity of the Radon transform, the basis combinations presented in equation (9) can be FBP (Filtered Backprojection) to form basis images, such as in the example presented in equation (10):

$$\hat{f}_1(r) + f_0(r) + c_{01} f_{01}(r) + c_{11} f_{11}(r) + c_{02} f_{02}(r) \quad (10)$$

In equation (10), the coefficients $c_{01}$, $c_{11}$, and $c_{02}$ can be found by the ABHC algorithm. Note that equation (10) provides one example equation that can be employed in ABHC techniques discussed herein, but in various embodiments, other equations can be employed, for example, by starting from equation (6) and using a different number of terms in the series expansion than in equation (7) to determine another polynomial equation.

The EBHC process discussed in greater detail above can be summarized as follows, for each image: (1) segment the image to a water image and a HAM image; (2) forward project the water image and the HAM image to obtain $P_0$ and $P_2$; (3) calculate the raw data combinations $P_0 P_2$ and $P_2^2$; (4) reconstruct the basis images $f_{11}$ and $f_{02}$, using FBP; and (5) construct the final corrected image, according to techniques discussed herein.

Figure 4:
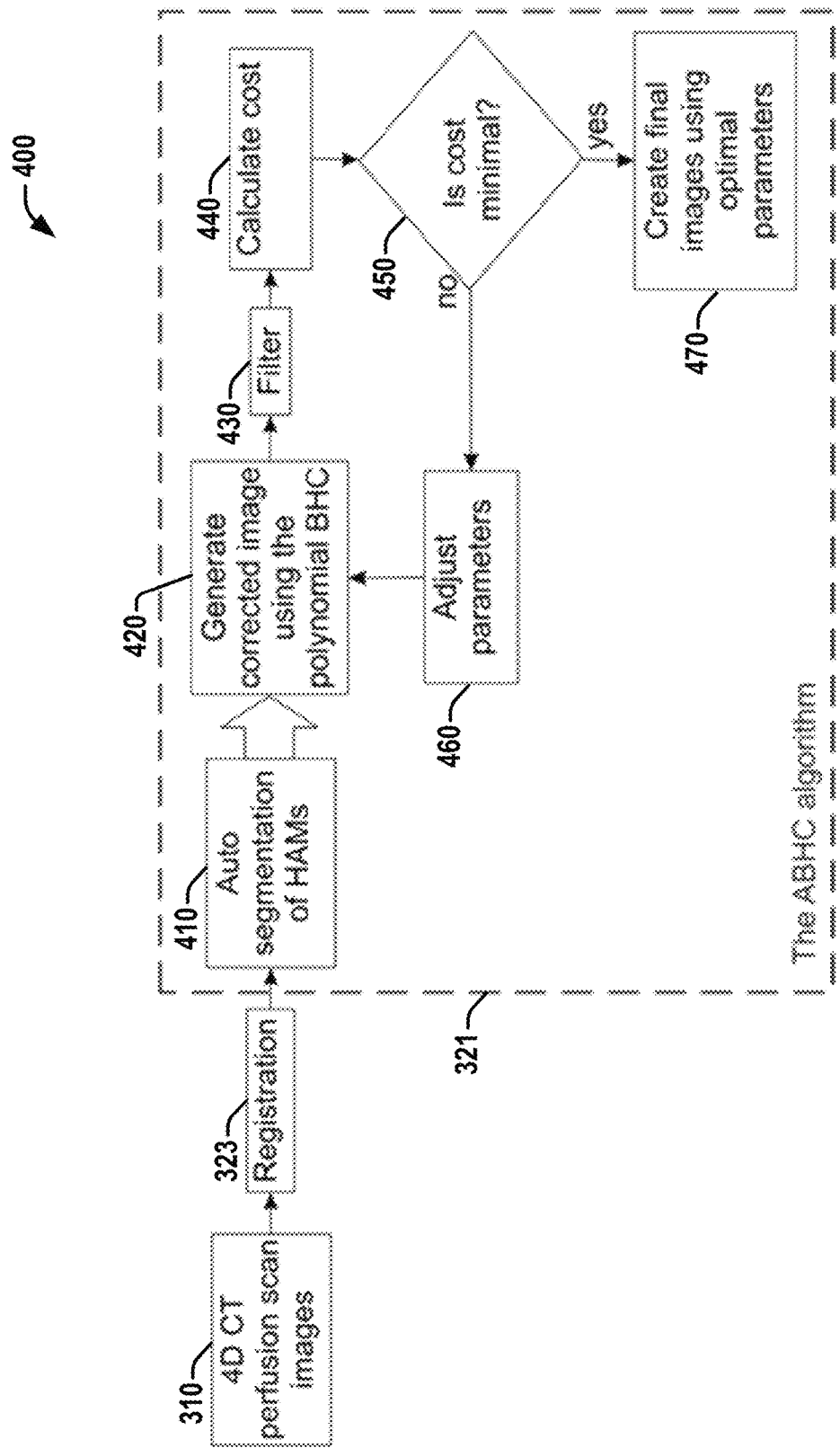
FIG. 4 illustrates a diagram of an example flow for an ABHC (Automated Beam Hardening Correction) technique, according to various aspects discussed herein.

Automated Beam Hardening Correction:

ABHC techniques discussed herein iteratively optimize a BHA (Beam Hardening Artifact)-sensitive cost function to estimate polynomial parameters to create BH-corrected image(s). Referring to FIG. 4, illustrated is a diagram showing an example flow 400 for an ABHC technique 321, according to various aspects discussed herein. As shown in FIG. 4, given images obtained (e.g., at 110, 210, or 310, etc.) that have been optionally registered (e.g., at 120, 230, or 323, etc.), ABHC can be performed (e.g., at 120, 220, or 321), which can begin by segmenting the highly attenuating materials (HAMs) by using a threshold at 410. ABHC can then apply the chosen BH correction algorithm (e.g., as discussed above in connection with EBHC) to an input image using initial parameters (e.g., values for parameters in equation (10) or other similar equation, as discussed above) at 420. The corrected image can then be filtered at 430, and a BH specific cost function can be evaluated at 440. If the cost is not minimal at 450, the algorithm iteratively adjusts (at 460) the BH correction algorithm parameters (e.g., repeating 420-60) until the cost is minimized. The final corrected image is generated using the optimized parameters at 470.

To apply ABHC to dynamic perfusion images, the images are first preprocessed. The cardiac volumes obtained over time are registered at 323 using a non-rigid registration method described above for ECG gated image acquisitions (for other tissues, distinct but similar image registrations can be employed that are appropriate for the tissue, or in some embodiments, registration can be omitted in non-cardiac imaging). Each volume is registered to the peak enhanced volume and ABHC correction parameters can be determined and applied in one of the following ways. According to a first technique, parameters can be estimated using a single image volume at peak enhancement and then those parameters can be used to correct all other images (ABHC-peak). Second, parameters can be estimated for each image containing iodine in the stack, and then the average of those parameters can be applied to the entire dataset (ABHC-average). Third, parameters can be estimated and applied for each image separately (ABHC-single).

Segmentation (e.g., of the LV cavity and myocardium for cardiac imaging) at 410, prior to calculation of the cost function (at 440), can be performed as follows. First, the registered time series can be analyzed to identify constant, high HU (Hounsfield Unit) structures (bones) (or structures high in some other relevant measurement, e.g., associated with a tracer, contrast agent, bubbles in ultrasound imaging, etc., depending on the imaging system employed), and structures that change intensity over time (iodine enhanced).

The bone and iodine masks can be obtained by thresholding the images. The standard deviation (SD) of each pixel over time can then be computed. Structures that are not enhanced with iodine will have a SD equivalent to the image noise. Structures that are slightly enhanced, like the myocardium, will have a higher SD. Structures with the highest SD are cavities that are filled with iodine, like the LV and aorta. Out of all the slices in the volume and over time, the slice with the largest sum of all temporally enhanced pixels will be the slice that presents the peak enhanced time point. On that slice, connected components can be applied to all structures having an SD above a threshold. The biggest structure will be the LV. Using connected components, the LV ca be found in other slices. To segment the myocardium, the LV mask can be dilated, and the original LV mask can be subtracted to get a 3D shell mask containing the myocardium. Then, only those pixels from the shell mask can be marked with an SD appropriate for the myocardium to obtain the segmented myocardium.

Noise reduction filtering at 430 is a beneficial preprocessing step that can be performed prior to computing the cost function at 440. High frequency noise, particularly textured streaks in reconstructed images, interferes with assessment of low frequency BH artifacts in the cost function. Different simple noise-reduction filters (Gaussian, median, and combinations) were experimented with, and their effects on BH corrections were determined. In various embodiments, any of a number of noise-reduction filters can be employed.

Cost Function:

Various embodiments can employ any of a variety of cost functions for ABHC. The cost function discussed below is one example of a cost function employable for CCTP imaging that is sensitive to BH artifacts that typically manifest as dark and bright regions in the image, as dark regions between two highly attenuating materials, and as cupping artifacts within homogeneous HAM regions. The example cost function consists of two terms, where the first term, $TV_{myo}$, addresses bright and dark artifacts in the myocardium and the second, $F_{LV}$, addresses cupping artifacts. The cost function is given by:

$$\psi(I_C(x,y|\theta)) = \alpha \cdot TV_{myo}(\hat{f}(I_C(x,y|\theta))) + (1-\alpha) \cdot F_{LV}(I_{C-LV}(x,y|\theta)) \quad (11)$$

where $\psi$ is the cost of the corrected image, $I_C(x,y|\theta)$, generated using the BH correction algorithm parameter vector $\theta$. The first and second terms in equation (11), assess streak artifacts and cupping, respectively. The coefficient $\alpha$ determines the relative weight of each term in the cost function. The first term is a measure of the total variation within the myocardium, $TV_{myo}$, which is computed using the total variation formula of equations (12):

$$G_x = \frac{\partial \hat{f}(I_C(x,y|\theta))}{\partial x}, G_y = \frac{\partial \hat{f}(I_C(x,y|\theta))}{\partial y} \quad (12)$$

$$G' = G_x^2 + G_y^2$$

$$TV_{myo}(\hat{f}(I_C(x,y|\theta))) = \sqrt{\sum_{myo} G'}/A_{myo}$$

G' is the gradient magnitude of G, and can be obtained by thresholding G such that all gradient values above a threshold are set to zero. This can be done in order to calculate the gradient only on relatively flat signals within the myocardium and not on high magnitude edges like those between the myocardium and the LV, or the myocardium and the air in the lungs. $A_{myo}$ is the area of the myocardium in pixels and is used to normalize $TV_{myo}$. The second term, $F_{LV}$, assesses cupping. Cupping is a phenomenon in CT images that manifests as artificial darkening towards the middle of homogeneous attenuating structures in an image. Using the segmented LV, the mean of the N (e.g., 20, or some other positive integer, etc.) highest HU values on the rim of the LV can be calculated and the average noise over the rim can be subtracted to obtain $LV_{max}$. The average noise can be subtracted in order to eliminate the bias that is introduced by choosing the N (e.g., 20, etc.) highest HU values. The rim of the LV is some positive integer number (e.g., 4, etc.) of pixels wide, along the circumference of the LV. The sum of square differences between every pixel in the LV can then be calculated to $LV_{max}$, as shown in equation (13):

$$F_{LV}(I_{C-LV}(x, y \mid \theta)) = \sqrt{\sum_{LV}(I_C(x, y \mid \theta) - LV_{max})^2} / A_{LV} \qquad (13)$$

where $A_{LV}$ is the area of the LV and is used to normalize the $F_{LV}$ term.

Although one specific example of an ABHC technique has been discussed for the purpose of illustration; in various embodiments, other ABHC techniques are possible. For example, the segmentation discussed above involved segmenting the image into two materials—the "water" image and the HAM image—and using those images to construct the base correction images. HAM components are usually bone and iodine, but in the segmentation discussed above, they are treated as one. In various embodiments, a more accurate technique can be employed, wherein the image is segmented into 3 material images: "water" image, bone image, and iodine image. This facilitates a more accurate treatment of bone and iodine, which allows consideration of each material's unique x-ray absorption characteristics and resulting BH properties. Additionally, in the example embodiment described above, the EBHC algorithm was used as the underlying BH correction algorithm. Although EBHC was provided as an example algorithm, ABHC can use any parametric, image-based BH correction algorithm. For example, EBHC could be replaced with a simple polynomial BH correction. Alternatively, the second order expansion in EBHC could be replaced with a higher order Taylor Series expansion.

Automated Beam Hardening Correction Using Machine Learning:

In various embodiments, instead of using three (or some other value, as discussed above) correction parameters over the whole range of projections, machine learning can be employed to find a tailored correction. Using the monoenergetic projection as the ground truth, a machine learning algorithm can find a much more accurate projection correction function. In this case, the input to the learning algorithm can be the projections from the polyenergetic scan and the target (correct) value can be the mono-energetic projection. Such embodiments can potentially create a much more accurate BH correction.

Robust Estimation of Flow and Derived Flow Measurements

Improved flow estimation can be provided by multiple techniques discussed herein. Various embodiments can employ one or more of the following techniques discussed in greater detail below: (1) a physiologically constrained model; (2) super-voxel CT perfusion clustering; (3) numerical implementation for superior flow estimation; FRIV (Flow Rate to fill the Intravascular Volume); and/or (4) confidence intervals.

Physiologically Constrained Model:

Various embodiments can employ a physiologically constrained flow estimation model (referred to herein as a Robust Physiological Model (RPM)) having a low number of free parameters that provides superior flow estimation to existing techniques. In various embodiments, tissue-specific models can be employed. In various cardiac embodiments, myocardial blood flow (MBF) is estimated by iteratively optimizing parameters until an estimated model time attenuation curve (TAC) in a tissue volume in the myocardium best fits the measured tissue TAC in a least squares sense. The model TAC, (Cm(t) (mg/mL)) is calculated by convolution of a measured AIF (Arterial Input Function), (Ca(t) (mg/mL)) (e.g., based on a relevant artery in the tissue (or LV in cardiac embodiments)), with the unitless model IRF (Impulse Residue Function) scaled by MBF, (RMBF(t) (mL/min/100 g)), and multiplied by a tissue density scaling, ($\rho$ (g/mL)). Note that Hounsfield Units in CT-MPI (and similarly with many other contrast agent/tracer related measures) change linearly with contrast agent concentration, allowing the use of HU values (etc.) directly after subtraction of a pre-contrast baseline value. Mathematically, this convolution is given by the integral of equation (14):

$$C_m(t_i) = \rho \int_{t_1}^{t_i} C_a(\tau) \cdot R_{MBF}(t_i - \tau) d\tau \qquad (14)$$

where $t_i$ is the time of a sampled data point ranging from time index i=1, 2, ..., N for N scans. In one example CCTP embodiment, $\rho$=1.05 g/mL, but this tissue density scaling can be changed as appropriate for various embodiments.

Figure 5:
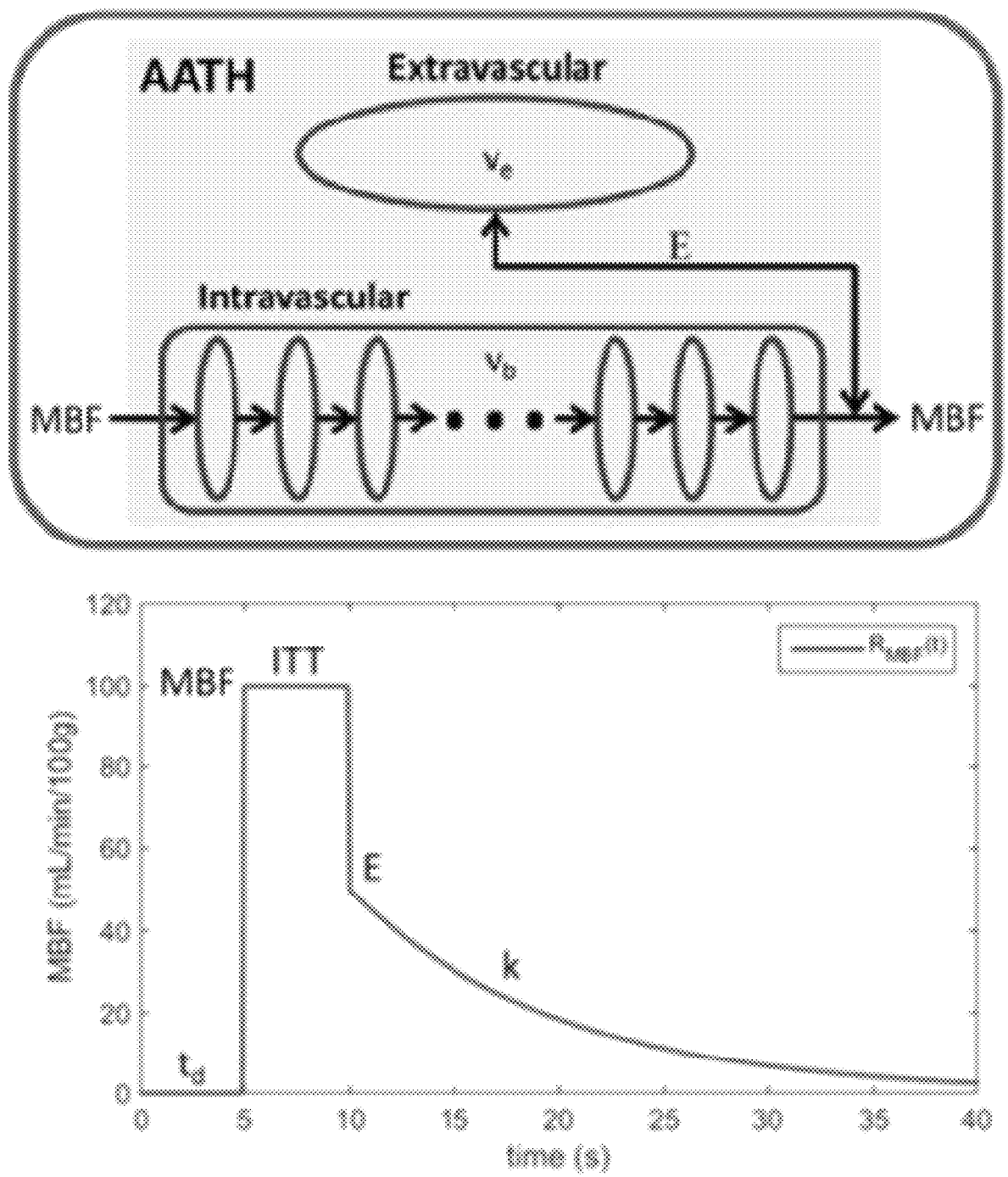
FIG. 5 illustrates a pair of diagrams showing a conceptual representation of the AATH (Adiabatic Approximation to the Tissue Homogeneity) model (top) and a graph of a corresponding Impulse Response Function (IRF), according to various aspects discussed herein.

In various embodiments, the robust physiological model can be based on the existing adiabatic approximation to the tissue homogeneity (AATH) model in which the observation region comprises intravascular and extravascular regions. AATH is also an approximation to the Johnson-Wilson model with five free parameters: $t_d$ (s), MBF (mL/min/100 g), ITT (s), E (unitless), and k ($s^{-1}$). Referring to FIG. 5, illustrated is a pair of diagrams showing a conceptual representation of the AATH (Adiabatic Approximation to the Tissue Homogeneity) model (top) and a graph of a corresponding Impulse Response Function (IRF), according to various aspects discussed herein. In the AATH model, as shown in the top of FIG. 5, contrast material passes into and through the intravascular space, exchanges with the well-mixed extravascular space, and exits the observation region. The corresponding IRF is given by equation (15):

$$R_{MBF}(t) = MBF \cdot \begin{cases} 0, & t < t_d \\ 1, & t_d \leq t < t_d + ITT \\ E \cdot \exp(-k(t - (t_d + ITT))), & t_d + ITT \leq t \end{cases} \qquad (15)$$

The robust physiologic model can use prior knowledge from the literature regarding the physiology of the tissue (e.g., microvascular physiology, etc.) and tracer/contrast agent (e.g., iodinated contrast agent, etc.) extravasation. For RPM in an example CCTP embodiment, E=0.6 and ITT=2 s. These values were selected when considering CT contrast agent extraction from the literature, which can range from E=0.3 to E=0.8, CT voxel size and capillary flow velocity, goodness-of-fit to preclinical data, and parameter estimability across imaging conditions. The example CCTP RPM model is defined with three free parameters: $t_d$, MBF, and k (in use cases involving other tissues, additional or alternative free parameters can be used to define the relevant RPM model).

Other embodiments are possible. In addition to the CCTP RPM model discussed above, there are other similar physiologic models with few free parameters that can be employed, such as the following example models. A first example model can employ a fixed E=0.6 and flow-dependent ITT=$\beta/\sqrt{MBF}$ where $\beta$ is a proportionality constant. This functional relationship between ITT and MBF is based on observations in the literature that MBF is a quadratic function of myocardial blood volume (MBV), MBF$\propto$MBV$^2$, and on the Central Volume Principle, ITT=MBV/MBF. A first example model can employ a fixed ITT=2 s but with E dependent on MBF according to the Renkin-Crone relationship: E=1−exp(−PS/MBF), where PS is the permeability surface area product. A third example model can employ an E and ITT that are both dependent on flow as described in the first and second example models. Some embodiments can employ a least-squared error as the objective function for the fitting model to the data. Other embodiments can employ other objective functions, for example, least weighted least squares, robust estimation approaches, maximum likelihood, maximum a posteriori (MAP) estimation, etc.

Super-Voxel Clustering for Perfusion (SCP):

Various embodiments can employ SCP, wherein image acquisition voxels are combined to form large super-voxels each having similar temporal characteristics and spatially constrained. Within a super-voxel, a robust central value can be determined at each time point using one of a variety of different methods described below. Super-voxel processing allows for rapid estimation of flow, since fewer time-attenuation curves are processed and superior flow estimates as effects of noise are significantly reduced. Because super-voxels combine image acquisition voxels having similar temporal characteristics and spatial connectivity, super-voxels are spatially and physiologically related. As a result, all clinical features of interest are preserved in the super-voxel process.

In various embodiments, super-voxels are generated by a perfusion-specific temporal clustering algorithm based on temporal and spatial proximity of voxels on CT perfusion data. For one slice of image data with N voxels and feature set with M temporal features, $f(x,y,l)=[f_{x,y}^1, f_{x,y}^2, \ldots f_{x,y}^l]$, where $f_{x,y}^1, f_{x,y}^2, \ldots f_{x,y}^l$ correspond to the time course features from the slice of image data at position (x,y) with feature index l=1, 2, . . . M. The approximate size of a super-voxel is N/k voxels, where k is an input parameter to determine the number of super-voxels to be generated. The cluster center $C_k=[f_{x,y}^1, f_{x,y}^2, \ldots f_{x,y}^M, x_k, y_k]^T$ can be initialized by sampling k regular grids with approximate interval $S=\sqrt{N/k}$. The search area for each cluster center is 2S×2S. The distance measure $D_S$ is given by equations (16):

$$d_{temporal} = \sqrt{\sum_{l=1}^{M} (f_c^l + f_i^l)^2}$$

$$d_{spatial} = \sqrt{(x_c - x_i)^2 + (y_c - y_i)^2}$$

$$D_S = \sqrt{d_{temporal}^2 + \left(\frac{d_{spatial}}{S}\right)^2 m^2}$$

(16)

where $d_{temporal}$ and $d_{spatial}$ correspond, respectively, to a temporal feature distance and a spatial distance between one cluster center c and a voxel i. The input parameter m facilitates weighting the relative importance between temporal and spatial distance. When m is large, super-voxels are more regular and compact. When m is small, super-voxels show less regular size and shape, but voxels in each region share more similar hemodynamic properties. In one example embodiment, different temporal features are analyzed for grouping different types of tissue (ischemic tissue, healthy tissue). Based on the analysis, the bolus arrival time (BAT) point (which is defined as the time point when the arterial input function (AIF) begins to rise) and the peak time of AIF can be calculated as two references for feature selection. In various embodiments, any of a variety of potential candidate features can be measured for each acquisition voxel, for example, one or more of: (1) mean HU (or other relevant measure for non-CT imaging systems) over all scans; (2) mean HU (etc.) from the first scan to BAT; (3) mean HU (etc.) from BAT to peak time of AIF; (4) mean HU (etc.) from peak time of AIF to the last scan; (5) standard deviation over all scans; (6) standard deviation from the first scan to BAT; (7) standard deviation from BAT to peak time of AIF; (8) standard deviation from peak time of AIF to the last scan.

In SCP, a feature selection process can be performed first (e.g., offline) and then applied to all future image datasets, or all future datasets until the feature selection process is repeated. Candidate features can be ranked (e.g., using the Maximum-Relevance-Minimum-Redundancy (mRMR) feature selection method) to identify a set of features for optimal grouping ischemic tissue and normal tissue. In feature selection, ROIs of healthy and ischemic tissue (e.g., myocardium) can be manually selected from animal data. In the example CCTP embodiment, 10,000 time-attenuation curve (TACs) with healthy labels and 10,000 TACs with ischemic labels were randomly selected from 2 pigs as the feature selection dataset, and candidate features were extracted. The following were selected as the top 3 features from mRMR ranking: (1) mean HU from BAT to peak time of AIF; (2) standard deviation over all scans; and (3) mean HU from peak time of AIF to the last scan.

Other embodiments and/or use cases can vary from the above in terms of one or more of feature generation and/or feature selection. As an example, additional features not listed above can be additionally or alternatively employed, for example, spatiotemporal features, skew, etc. Another possible difference is that other methods for rank ordering features, such as the Wilcoxon rank-sum test, can be employed. The number of features employed for SCP can also vary, either by employing a greater number of features or a lesser number of features.

Following feature selection, SCP can be applied to generate super-voxels and blood flows (e.g., MBFs) in 4D perfusion data (e.g., CT perfusion data). Within each super-voxel, a central determination of the HU (etc.) value over the voxels comprising the super-voxel can be extracted. Optionally, a robust estimator such as a 10% trimmed mean (e.g., or N % trimmed mean for other values of N, etc.) can be used, whereby the lowest 10% and the highest 10% of voxel values are discarded prior to averaging results. Employing a trimmed mean can facilitate robust estimation of the central value by excluding outliers. By retaining 80% (etc.) of values, the average value reduces effects of noise. In other embodiments, a different robust estimator such as median can be used.

Once time-attenuation curves for super-voxels are determined, any of a variety of techniques can be employed for assessing perfusion blood flow. Various embodiments can employ a RPM for perfusion assessment, discussed in greater detail above. Once perfusion flows are estimated for super-voxels, regional assessments and visualizations can be made, as described in connection with method 200 and/or processing pipeline of method 300, discussed above.

In various embodiments, other techniques can be employed. As examples, super-voxel can be extended to group 3D data, other temporal features such as skewness and kurtosis can be included, region merging algorithms can be applied to determine the optimal number of super-voxels on each slice automatically, etc.

In various embodiments, other blood flow (e.g., MBF) estimation methods such as SVD (Singular Value Decomposition) and other model-based methods can additionally or alternatively be applied to estimate the blood flow (e.g., MBF) on each super-voxel. The process of creating perfusion super-voxels over a temporal sequence of 3D volumes can employ a method applicable to static color images using "simple linear iterative clustering" or SLIC.

Numerical Implementation for Superior Flow Estimation:

In various embodiments, blood flow (e.g., MBF) can be estimated by iteratively optimizing parameters until an estimated model time attenuation curve (TAC) best fits the measured tissue TAC in a least squares sense. The convolution can be implemented using a semi-analytic approach introduced herein. The approach employable in various embodiments can minimize numerical errors which can appear in other methods, such as discrete convolution. In the semi-analytic approach discussed herein, the arterial input can be expressed as a piecewise polynomial, which can be a sequence of polynomials defined for adjacent time intervals to pass through the measured data values. The model output is a sum of the convolution integrals, one for each polynomial piece. Each convolution integral can be calculated by analytically integrating the product of the polynomial and the impulse response for a selected model. In one example implementation, first-order polynomials can be used to make a linear spline, equivalent to linear interpolation between measured data points, as in equations (17):

$$C_a(t) = a_i + b_i \cdot (t - t_i), \quad t_i \leq t \leq t_{i+1} \tag{17}$$

$$a_i = C_a(t_i)$$

$$b_i = \frac{C_a(t_{i+1}) - C_a(t_i)}{t_{i+1} - t_i}$$

where $a_i$ is the constant coefficient in the linear equation, $b_i$ is first-order coefficient or slope, and $t_i$ is the time of a sampled data point ranging from time index i=1, 2, ..., N for N scans. The example embodiment employs a linear spline rather than higher-order splines to avoid oscillations (e.g., under- or overshoot) between sampled data points and as a tradeoff between computational efficiency and accuracy given the typical noise levels in the data (in various embodiments, higher-order polynomial splines can be employed). Using this approach, the linear spline from equations (16) can be substituted for Ca(t) in the convolution, equation (1), giving the model output corresponding to the impulse response RMBF(t) of equation (18):

$$C_m(t) = \sum_{j=1}^{N-1} \left[ \int_{t_j}^{t_{j+1}} (a_j + b_j \cdot (\tau - t_j)) \cdot \rho \cdot R_{MBF}(t - \tau) d\tau \right] \tag{18}$$

where the index j denotes the lower bounded time index for each piece of the linear spline and index j+1 represents the upper bounded time index and t is on the interval $t_1 \leq t \leq t_N$. Each integral has a closed-form analytic solution whose form depends on the impulse response model used. The model TAC ($C_m$) was compared to the measured tissue curve ($C_t$) at sample times $t_i$ using the unweighted sum-of-squared differences objective function, as in equation (19):

$$\Phi = \sum_{i=1}^{N} (C_m(t_i) - C_t(t_i))^2 \tag{19}$$

which is minimized when the model curve has reached an optimal fit to the data set across all N scans.

In various embodiments, a gradient-based optimization algorithm can be used to minimize Φ in equation (19) with respect to model parameters. For robust and efficient performance, analytically-determined gradients can be supplied. First, the objective function can be differentiated with respect to each model parameter, $\theta_s$, as in equation (20):

$$\frac{\partial \Phi}{\partial \theta_s} = 2 \sum_{i=1}^{N} \frac{\partial C_m(t_i)}{\partial \theta_s} \cdot (C_m(t_i) - C_t(t_i)) \tag{20}$$

where $C_m(t_i)$ is the model output and $\partial C_m(t_i)/\partial \theta_s$ is the dynamic sensitivity function of the model-predicted TAC with respect to parameter $\theta_s$. The sensitivity function can be computed in a similar fashion as $C_m(t)$, as in equation (21):

$$\frac{\partial \Phi}{\partial \theta_s} = 2 \sum_{i=1}^{N} \frac{\partial C_m(t_i)}{\partial \theta_s} \cdot (C_m(t_i) - C_t(t_i)) \tag{21}$$

where the derivative $$\frac{\partial R_{MBF}(t_i - \tau)}{\partial \theta_s}$$

is derived analytically from the model impulse response function.

Various embodiments can employ different techniques for flow estimation. The example embodiment discussed above used the interior-point algorithm for optimization. In various embodiments, other embodiment techniques such as Nelder-Mead simplex, genetic algorithm, or particle swarm can be used for optimization. Additionally, this example embodiment used the RPM model discussed herein, but other similar physiological embodiments can be used in various embodiments (e.g., the adiabatic approximation to the tissue homogeneity (AATH) model). Blood flow (e.g., MBF) estimation can be done in large sub-volumes of interest in the tissue (e.g., myocardium) that are identified manually or automatically; in super-voxels, as discussed above; or in each individual voxel location.

Flow Rate to fill the Intravascular Volume (FRIV):

Various embodiments can employ FRIV, another metric discussed herein, which is very sensitive to flow deficits, providing flow maps having very good signal to noise ratio. FRIV can describe the rate at which blood flows from the arterial input function site to fill the intravascular space (e.g. capillaries, arterioles) of the tissue (e.g., myocardium). FRIV can be computed by taking the tissue (e.g., myocardial) blood volume (e.g., MBV), which is related to MBF and ITT by MBV=MBF*ITT and dividing it by the total amount of time taken to fill the tissue blood volume (e.g., MBV), $t_d$+ITT. This gives equation (22):

$$FRIV = \frac{MBF \cdot ITT}{t_d + ITT} \tag{22}$$

Unlike existing metrics, FRIV includes the delay time, $t_d$, from the arterial input function site to the site of interest.

Figure 6:
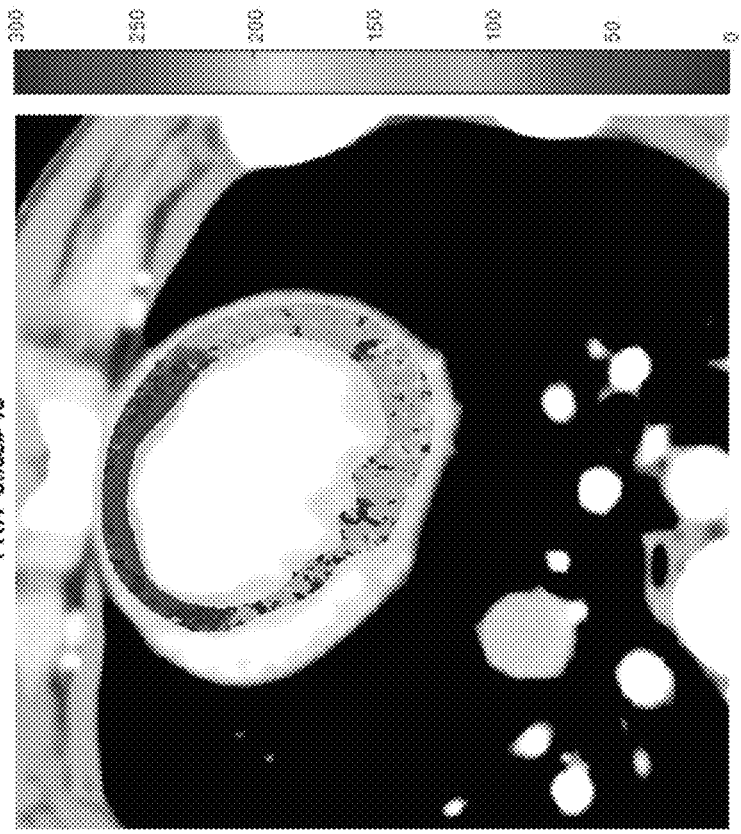
FIG. 6 illustrates example images of Myocardial Blood Flow (MBF) on the left and the same image of MBF (right) after FRIV (Flow Rate to Fill the Intravascular Volume) calculation with reduced noise, according to various embodiments discussed herein.
Figure 6:
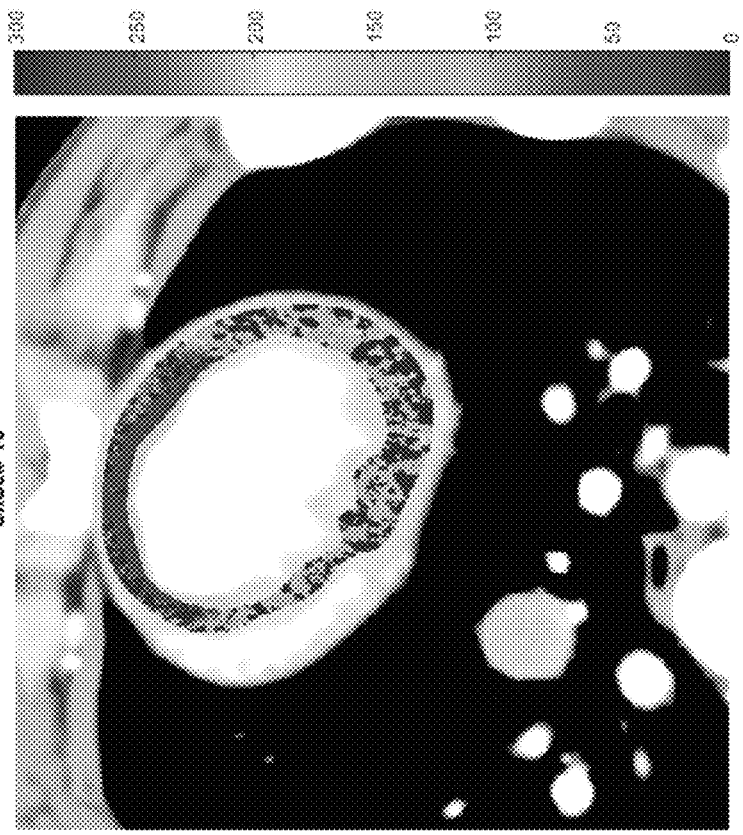

Since $t_d$ depends upon flow rate within the intervening vasculature, FRIV becomes a sensitive marker for a regional flow deficit and for an absolute flow marker. Similar processing methods can additionally or alternatively be employed in various embodiments. In one example embodiment, portions of the model estimated impulse response function can be integrated over to obtain measures of contrast agent retention that are sensitive to perfusion defects. FRIV greatly improves analysis of models with more than three free parameters. Referring to FIG. 6, illustrated is a diagram showing example images of MBF (left) and the same image of MBF after FRIV having reduced noise, according to various embodiments discussed herein.

Blood Flow Confidence Intervals:

Various embodiments can provide estimates of blood flow (e.g., MBF). Estimating the blood flow (e.g., MBF) confidence interval (e.g., MBFCI) can give clinicians the ability to know if a region has a statistically significant flow deficit. MBFCI (etc.) can be calculated using the empirical likelihood technique. In various embodiments, a 95% confidence can be used, corresponding to $\alpha=0.05$ and $1-\alpha=0.95$ (95% is widely used for determination of statistical significance, but in various embodiments, other values can be used instead). The technique can involve first calculating the joint confidence region which encompasses all parameter combinations that fit the measured data within a 95% (etc.) confidence limit. This can generate the joint confidence region, $R(\theta)$, which is defined as all parameter combinations $\theta$ that satisfy the relationship in equation (23):

$$\{R(\theta):\Phi(\theta) \le \sigma^2 \chi_n^{2,1-\alpha}\} \quad (23)$$

where the noise can be estimated as in equation (24):

$$\sigma^2 \approx \frac{\Phi(\theta_{opt})}{n} \quad (24)$$

where $\Phi(\theta_{opt})$ comes from the best fit parameters determined by the optimization algorithm, and $\chi_n^{2,1-\alpha}$ is the chi-squared value for the $(1-\alpha)$ probability given n degrees of freedom, where n is the number of measurement time points. This calculation for the joint confidence region assumes that errors between the model and measurements are due to uncorrelated, normally distributed noise with constant variance $\sigma^2$ at all measurement times and that $\sigma^2$ represents deviations due only to noise. $R(\theta)$ can be computed by sampling a j-dimensional grid of parameter combinations where j is the number of estimated parameters (e.g., combinations of $t_d$, MBF (or other blood flow), and k for RPM and combinations of $t_d$, MBF (etc.), ITT, E, and k for AATH).

Once the joint confidence region is known, the maximum blood flow (e.g., maximum myocardial blood flow, $MBF_{max}$), and minimum blood flow (e.g., minimum myocardial blood flow, $MBF_{min}$) contained in $R(\theta)$ can be determined. The range between the maximum blood flow (e.g., maximum myocardial blood flow, $MBF_{max}$), and minimum blood flow (e.g., minimum myocardial blood flow, $MBF_{min}$) describes the uncertainty in MBF at the 95% (etc.) confidence level. For a myocardial blood flow example, this is given by equation (25):

$$MBF_{CI}=(MBF_{max}, MBF_{min}) \quad (25)$$

Figure 7:
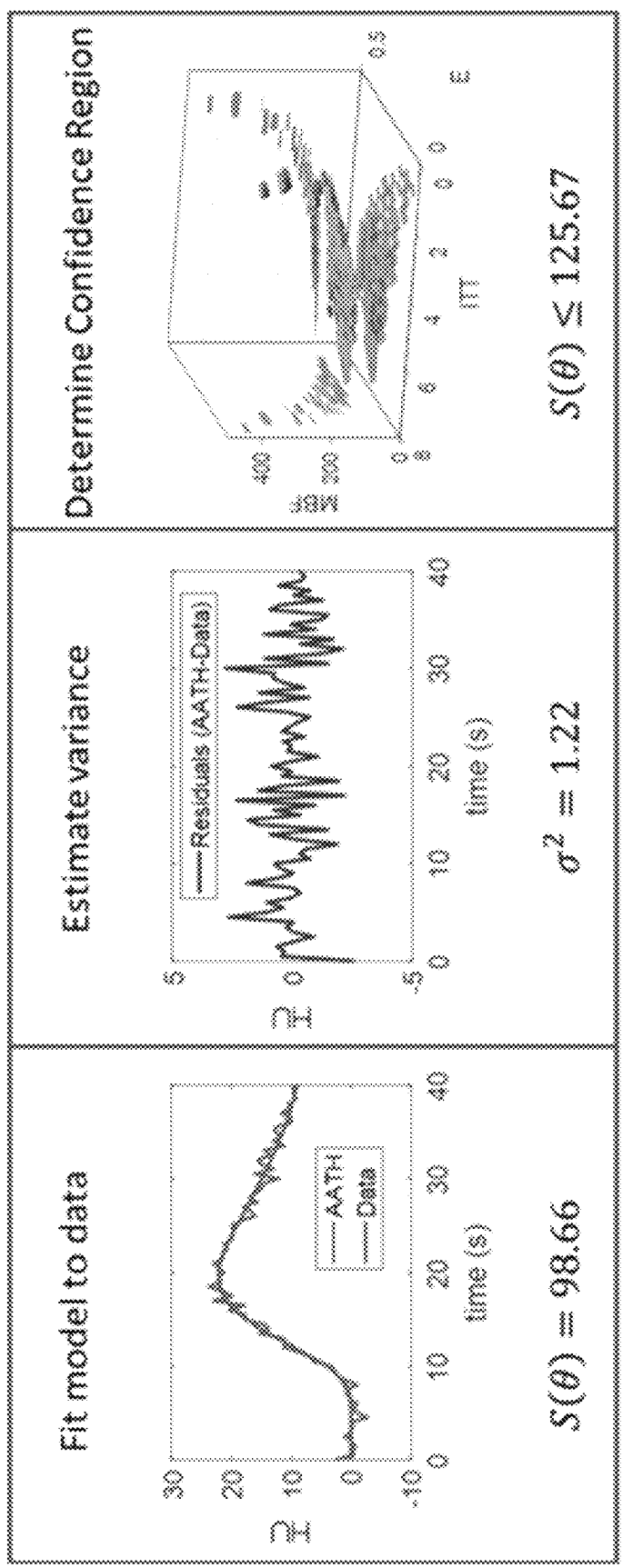
FIG. 7 illustrates a diagram showing an example application of an empirical likelihood technique, according to various embodiments discussed herein.

Referring to FIG. 7, illustrated is a diagram showing an example application of an empirical likelihood technique, according to various embodiments discussed herein. First, the model can be fit to data to find the optimal model parameters and minimum sum of squared differences. The variance of the residuals can be calculated and used in equation (24). The joint confidence region can be determined by finding all parameter combinations within the grid search space that satisfy the relationship in equation (23). In FIG. 7, a 3D joint confidence region is visualized in the leftmost graph, and projections onto parameter planes are visualized as shadows which correspond to 2D joint confidence regions.

Figure 8:
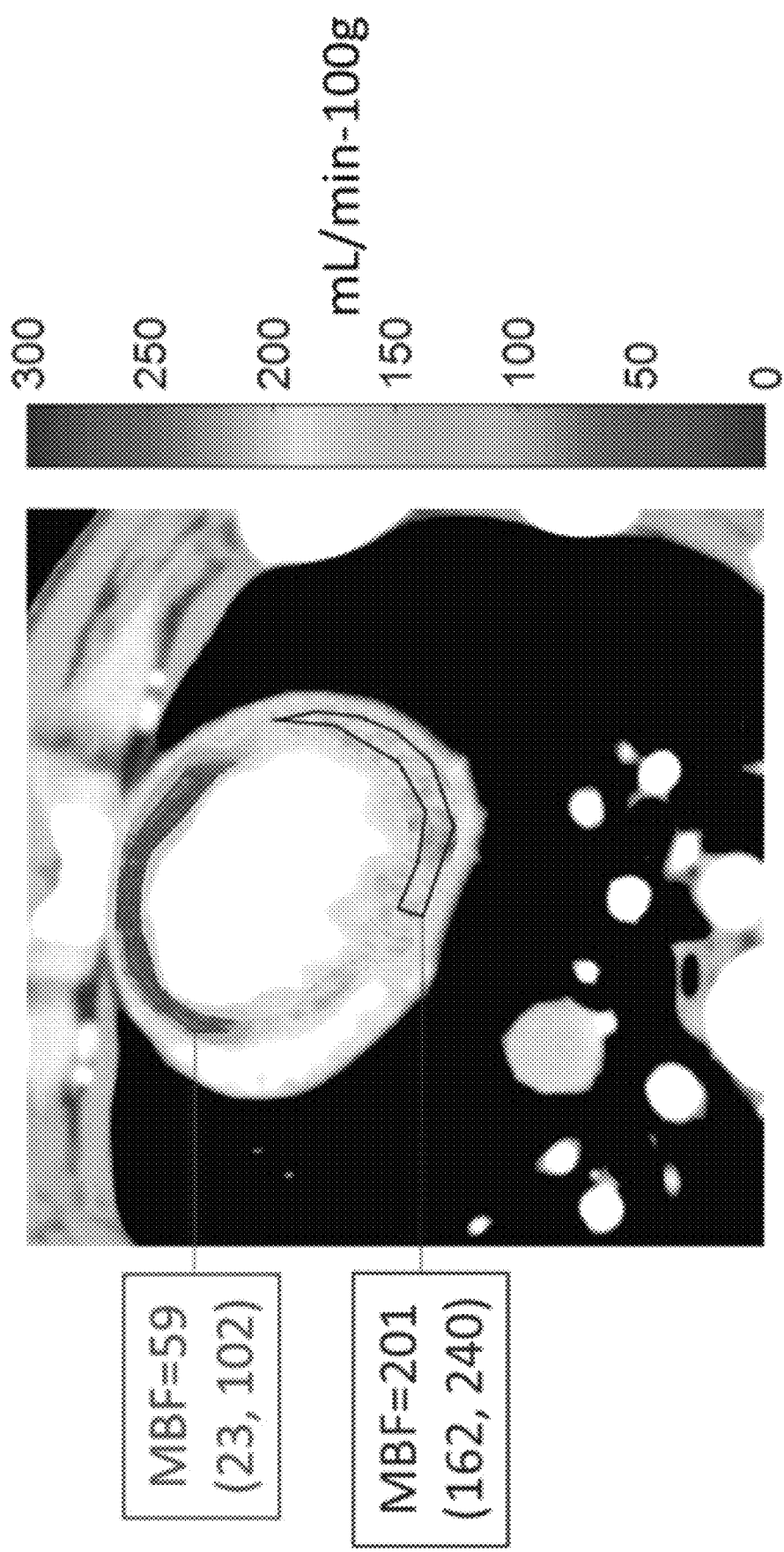
FIG. 8 illustrates diagram showing a representative MBF map and $MBF_{CI}$ (MBF confidence interval) in ischemic and healthy myocardium, according to various embodiments discussed herein.

Referring to FIG. 8, illustrated is a diagram showing a representative MBF map and $MBF_{CI}$ in ischemic and healthy myocardium, according to various embodiments discussed herein. FIG. 8 shows a quantitative MBF map with average MBF indicated in the ischemic myocardium (the upper ROI) and healthy myocardium (the lower ROI). The lower and upper $MBF_{CI}$ bounds are given in parenthesis for each ROI. For the ischemic region (upper ROI), for example, the 95% confidence interval ranges between 23 mL/min-100 g to 102 mL/min-100 g, which is distinct from the confidence interval of the healthy region (lower ROI), which ranges from 162 mL/min-100 g to 240 mL/min-100 g.

Various embodiments can provide features and advantages not available in existing systems.

Processing Pipeline:

Image processing pipeline methods (e.g., according to any of methods 100, 200, or 300, etc.) discussed herein can yields accurate registration of imaging (e.g., CT, etc.) volumes across time, which can facilitate accurate flow measurements. Additionally, such methods can provide for accurate identification of specific tissues (e.g., myocardium, etc.) which can enable automated determination of arterial input function and accurate delineation of a tissue (e.g., myocardial, etc.) flow map.

Automated Beam Hardening Correction:

For CT-related embodiments, ABHC techniques discussed herein provide multiple advantages. For example, they can eliminate a need for calibration experiments required by existing systems, and are independent of both the scanner and scanner configuration (e.g., slice thickness, number of channels, kVp, etc.). Additionally, such techniques can facilitate dynamic perfusion measurements, which is the most demanding procedure for beam hardening correction. Although specific algorithms are discussed herein as examples in connection with ABHC, it can be employed with multiple beam hardening correction algorithms, and can use multiple methods and chose the one giving the best solution, as in one example embodiment created in testing aspects discussed herein (such embodiments can, however, be computationally intensive). Finally, ABHC techniques according to various embodiments discussed herein can provide fully automated beam hardening correction.

Robust Estimation of Flow and Derived Flow Measurements:

Various techniques discussed herein for estimating perfusion-related quantities can provide multiple features and advantages. First, embodiments discussed herein can facilitate derivation of perfusion measurements via aggregation of super-voxels for CT perfusion. Additionally, these techniques can comprise incorporation of physiologic constraints (e.g., via a model such as the RPM discussed above, AATH, etc.) to aid flow estimation, application of improved computational methods as discussed above, and determination of metrics not available via existing systems (e.g., FRIV, etc.).

Flow Confidence Intervals:

Various embodiments discussed herein can facilitate determination of confidence intervals associated with flow and derived flow measurements discussed herein. Flow confidence intervals generated by various embodiments discussed herein can allow physicians to know if they are obtaining significant results, unlike existing assessments (e.g., visual goodness of fit), which do not allow physicians to know the reliability of flow measurements.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, or 400, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to system-independent perfusion imaging facilitate determination of flow measurements that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 9:
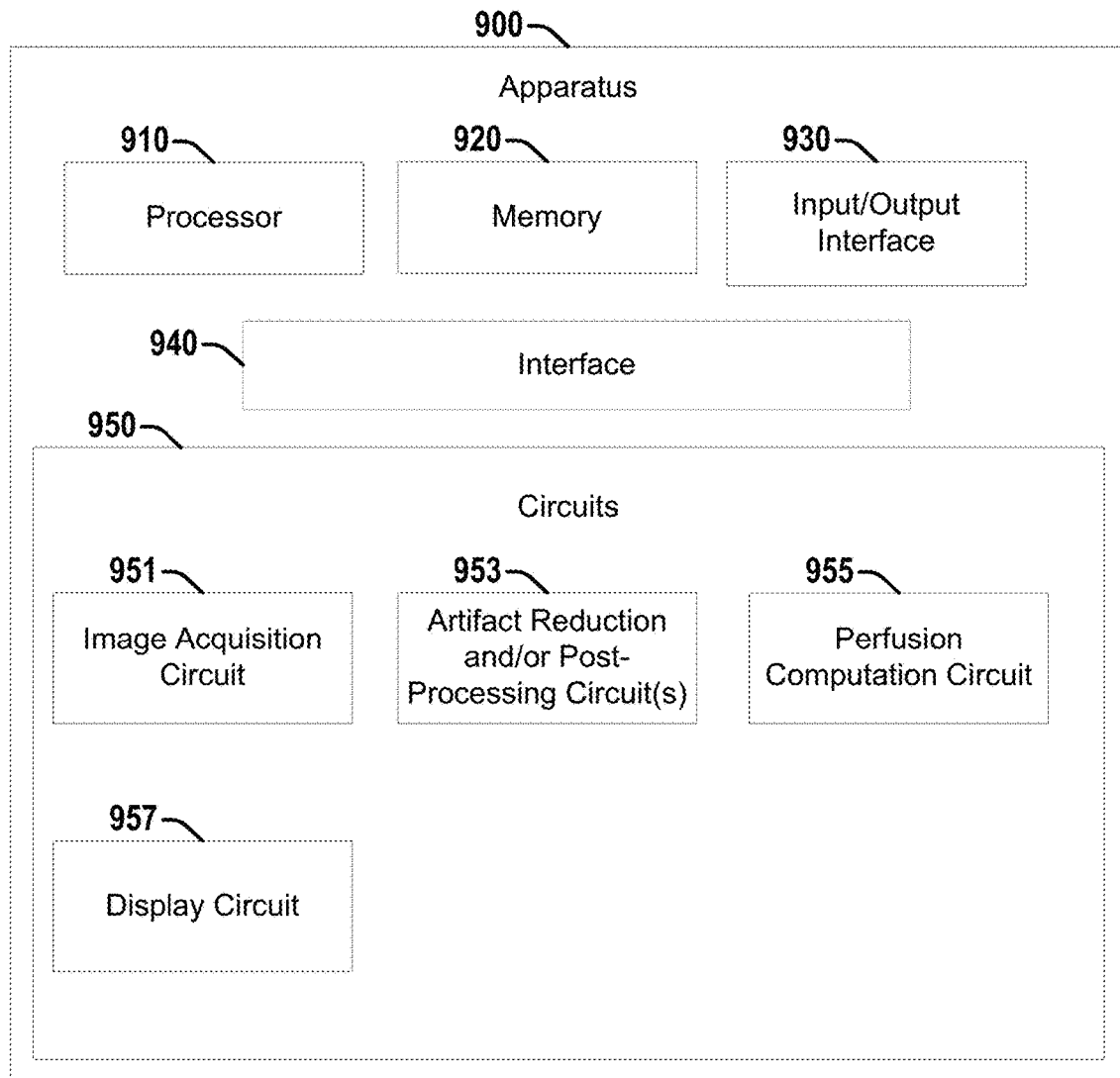
FIG. 9 illustrates a diagram of a first example apparatus that can facilitate system-independent perfusion imaging according to various embodiments discussed herein.

Referring to FIG. 9, illustrated is a diagram of a first example apparatus 900 that can facilitate system-independent perfusion imaging according to various embodiments discussed herein. Apparatus 900 can be configured to perform various techniques discussed herein, for example, one or more of processing pipelines discussed herein, ABHC techniques, calculation of flow and/or other quantitative perfusion measurements, and/or estimation of flow confidence intervals. Apparatus 900 comprises a processor 910. Apparatus 900 also comprises a memory 920. Processor 910 can, in various embodiments, comprise circuitry such as, but not limited to, one or more single-core or multi-core processors. Processor 910 can include any combination of general-purpose processors and dedicated processors (e.g., graphics processors, application processors, etc.). The processor(s) can be coupled with and/or can comprise memory (e.g. memory 920) or storage and can be configured to execute instructions stored in the memory 920 or storage to enable various apparatus, applications, or operating systems to perform operations and/or methods discussed herein. Memory 920 can be configured to store perfusion-related imaging data of tissue. The imaging data can have a plurality of voxels, each voxel having an associated intensity (with 2D slices comprising a plurality of pixels, with each pixel having an associated intensity), and can comprise original images and/or images after one or more of pre-processing, artifact reduction, segmentation, etc. In some aspects (e.g., ABHC using machine learning), memory 920 can be further configured to store a training set of images and/or a testing set of images. Memory 920 can be further configured to store one or more of quantitative perfusion measurements derived from imaging data or confidence intervals associated with perfusion measurements.

Apparatus 900 also comprises an input/output (I/O) interface 930 (e.g., associated with one or more I/O devices), a set of circuits 950, and an interface 940 that connects the processor 910, the memory 920, the I/O interface 930, and the set of circuits 950. I/O interface 930 can be configured to transfer data between memory 920, processor 910, circuits 950, and external devices, for example, a CT system or a cancer recurrence prediction system.

The set of circuits 950 can comprise an image acquisition circuit 951, an artifact reduction and post-processing circuit 953, a perfusion computation circuit 955, and a display circuit 957. Image acquisition circuit 951 is configured to access a set of perfusion images of a tissue (e.g., cardiac CT perfusion images, MRI images, PET images, SPECT images, ultrasound images, etc.). The perfusion imaging data can comprise a time ordered set of 3D stacks of images, each 3D stack having a plurality of plurality of voxels, each voxel having an associated intensity (with 2D slices comprising a plurality of pixels, with each pixel having an associated intensity). In one embodiment, the radiological images comprise 4D CT perfusion image data. In one embodiment, the 4D CT perfusion image data comprises 3D stacks of DICOM CCTP images over time. In another embodiment, other types of radiological images and/or radiological images of other tissues can be accessed or employed. Accessing the radiological images can comprise accessing a radiological images stored in memory 920. In one embodiment, accessing the radiological images can include accessing a radiological image stored in a data storage device, including a hard disk drive, a solid state device, a tape drive, or accessing a radiological image over a local area network. Accessing the radiological images can comprise acquiring electronic data, reading from a computer file, receiving a computer file, reading from a computer memory, or other computerized activity not practically performed in the human mind.

Artifact reduction and post-processing circuit 953 is configured to perform one or more artifact reduction and post-processing techniques discussed herein. For example, for CT image data, artifact reduction and post-processing circuit 953 can be configured to perform ABHC to reduce beam hardening artifacts in images. As another example, artifact reduction and post-processing circuit 953 can perform 3D registration of images to reduce or eliminate motion artifacts. In a further example, artifact reduction and post-processing circuit 953 can correct for partial scan artifacts. As an additional example, artifact reduction and post-processing circuit 953 can apply axis reformatting to images to align image data with a preferred axis (e.g., short axis for cardiac images, long axis of a tumor, etc.). As a final example, artifact reduction and post-processing circuit 953 can perform or facilitate tissue segmentation of image data (e.g., myocardium, LV, etc.). In various embodiments, artifact reduction and post-processing circuit 953 can comprise separate circuitry for each of these artifact reduction and/or post-processing acts, or one or more artifact reduction and/or post-processing acts can be performed by common circuitry.

Perfusion computation circuit 955 is configured to compute one or more quantitative perfusion measurements and/or estimate confidences associated with at least one quantitative perfusion measurements. For example, perfusion computation circuitry 955 can compute blood flow (e.g., MBF, etc.) and/or other quantitative perfusion measurements (e.g., FRIV, etc.). As an additional example, perfusion computation circuitry 955 can estimate confidence intervals for blood flow and/or other quantitative perfusion measurements. Perfusion computation circuitry 955 can output computed measurements and/or estimated confidence intervals, and/or modified perfusion images that indicate one or more quantitative perfusion measurements and/or confidence intervals. In various embodiments, perfusion computation circuitry 955 can comprise separate circuitry for each of these perfusion computation and/or confidence estimation acts, or one or more perfusion computation and/or confidence estimation acts can be performed by common circuitry.

Display circuit 957 is configured to display modified perfusion image(s) that indicate blood flow and/or other quantitative perfusion measurements, and/or confidence estimates for quantitative perfusion measurements. Display circuit 957 can perfusion information in a variety of ways, such as perfusion measurements (e.g., blood flow, ratio of stress blood flow to rest blood flow, etc.) mapped onto a physiological 2D image, or as a 3D visualization, etc. (e.g., via color-coding, etc.); confidence estimates on perfusion image data, etc.

Figure 10:
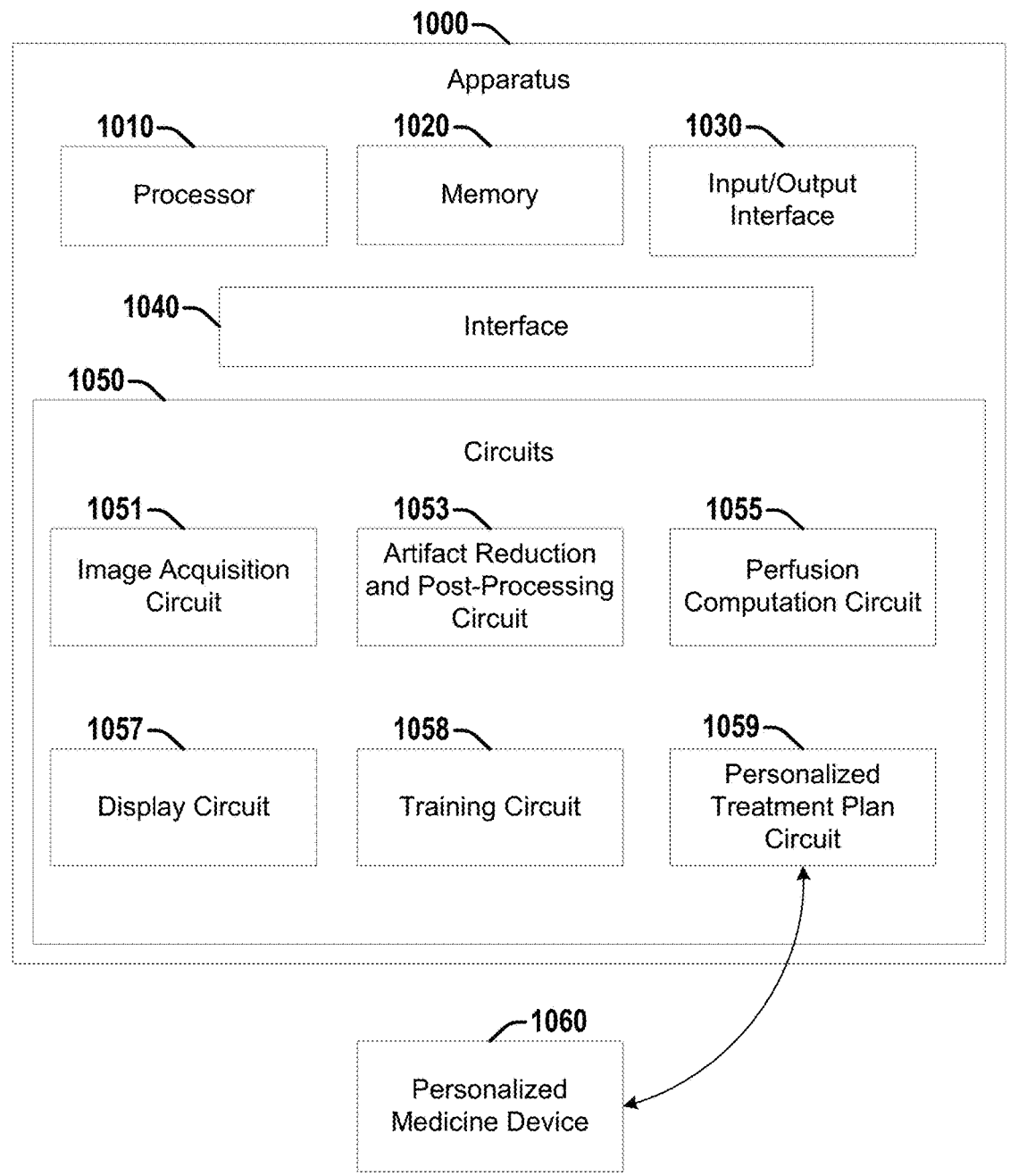
FIG. 10 illustrates a diagram of a second example apparatus that can facilitate system-independent perfusion imaging according to various embodiments discussed herein.

Referring to FIG. 10, illustrated is a diagram of a second example apparatus 900 that can facilitate system-independent perfusion imaging according to various embodiments discussed herein. Example apparatus 1000 is similar to the example apparatus of FIG. 9 (e.g., with elements 1010-1057 corresponding to elements 910-957, etc.), but comprises additional details and elements. In one embodiment, apparatus 1000 comprises a training circuit 1058. In some aspects, training circuit 1058 can be configured to train artifact reduction and post-processing circuit 1053, a machine learning classifier, including a LDA, to determine tailored ABHC and/or to perform automated tissue segmentation. In one embodiment, training circuit 1058 can obtain, as input to a learning algorithm, projections from a polyenergetic scan, wherein the target (correct) value can be a mono-energetic projection. Based on this, training circuit 1058 can determine a projection correction function for ABHC having improved accuracy. In another embodiment, training circuit 1058 can obtain, for a given tissue, a training set of expert-segmented images of that tissue, and can be trained to perform segmentation of that tissue in an automated or semi-automated manner. In further embodiments, training circuit 1058 can be trained, for each of one or more tissues based at least in part on a training set of modified perfusion image data correlated with diagnoses (e.g., positive or negative, or in more than 2 categories, etc.) and/or prognoses related to one or more medical conditions associated with that tissue (e.g., cardiac (e.g., coronary artery disease, microvascular disease, etc.), brain, tumor types, etc.), and can classify modified perfusion images received from perfusion computation circuitry 1055 based on categories associated with those diagnoses and/or prognoses.

Apparatus 1000 can also comprise personalized treatment plan circuit 1059. Personalized treatment plan circuit 1059 can be configured to generate a personalized treatment plan based, at least in part, on classification(s) obtained from training circuit 1058. Personalized treatment plan circuit 1059 can be further configured to generate a personalized treatment plan based on modified perfusion images and associated classification(s). Personalized treatment plan circuit 1059 can be configured to generate a personalized treatment plan for the patient of whom the perfusion images were acquired based, at least in part, on the classification(s), the perfusion images, and/or one or more quantitative perfusion measurements derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, (e.g., for tumor-related embodiments) a chemotherapy agent dosage or schedule, and/or other treatments.

Apparatus 1000 further comprises personalized medicine device 1060. Apparatus 1000 can be configured to provide the classification(s), modified perfusion images, quantitative perfusion measurements and/or confidence estimates, or other data to personalized medicine device 1060. Personalized medicine device 1060 may be, for example, a computer assisted diagnosis (CADx) system or other type of personalized medicine device that can be used to facilitate the prediction of disease recurrence. In one embodiment, personalized treatment plan circuit 1059 can control personalized medicine device 1060 to display a personalized treatment plan, modified perfusion images, quantitative perfusion measurements and/or confidence estimates, or other data on a computer monitor, a smartphone display, a tablet display, or other displays.

Examples herein can include subject matter such as an apparatus, a quantitative perfusion measurement system, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing 4D (Four Dimensional) perfusion imaging data of a tissue, where the 4D perfusion imaging data comprises a plurality of 3D (Three Dimensional) stacks of perfusion imaging data over time; performing at least one of artifact reduction or post-processing on the 4D perfusion image data to generate processed 4D perfusion image data; computing one or more quantitative perfusion parameters for the tissue based at least in part on the processed 4D perfusion image data; and outputting a visual representation of the one or more quantitative perfusion parameters.

Example 2 comprises the subject matter of any variation of any of example(s) 1, wherein the 4D perfusion imaging data comprises one of 4D CT (Computed Tomography) perfusion imaging data, 4D MRI (Magnetic Resonance Imaging) perfusion imaging data, 4d ultrasound perfusion imaging data, 4D PET (Positron-Emission Tomography) perfusion imaging data, or 4D SPECT (Single-Photon Emission Computed Tomography) perfusion imaging data.

Example 3 comprises the subject matter of any variation of any of example(s) 2, wherein the 4D perfusion imaging data comprises the 4D CT perfusion imaging data, and wherein performing at least one of artifact reduction or post-processing comprises performing Automated Beam Hardening Correction (ABHC) on the 4D perfusion imaging data to reduce beam hardening artifacts in the 4D perfusion imaging data.

Example 4 comprises the subject matter of any variation of any of example(s) 3, wherein performing ABHC on the 4D perfusion imaging comprises iteratively adjusting one or more ABHC correction parameters of an ABHC correction model to minimize an ABHC cost function.

Example 5 comprises the subject matter of any variation of any of example(s) 4, wherein the ABHC correction model is one of an Empirical Beam Hardening Correction (EBHC) model or a polynomial Beam Hardening (BH) correction model.

Example 6 comprises the subject matter of any variation of any of example(s) 1-5, wherein performing at least one of artifact reduction or post-processing comprises minimizing motion between frames of the 4D perfusion imaging data via 3D registration of the frames.

Example 7 comprises the subject matter of any variation of any of example(s) 1-6, wherein performing at least one of artifact reduction or post-processing comprises correcting for partial scan acquisitions and reconstructions.

Example 8 comprises the subject matter of any variation of any of example(s) 1-7, wherein performing at least one of artifact reduction or post-processing comprises reducing the effect of fluctuations from partial scan artifacts via applying a spatio-temporal filter to the 4D perfusion imaging data.

Example 9 comprises the subject matter of any variation of any of example(s) 1-8, wherein performing at least one of artifact reduction or post-processing comprises, for each 3D stack of the plurality of 3D stacks of perfusion imaging data, reformatting axial slices of that 3D stack to a selected axis.

Example 10 comprises the subject matter of any variation of any of example(s) 1-9, wherein performing at least one of artifact reduction or post-processing comprises segmenting the tissue via applying smooth contours to the 4D perfusion imaging data based on a plurality of user-defined points.

Example 11 comprises the subject matter of any variation of any of example(s) 1-10, wherein computing one or more quantitative perfusion parameters for the tissue comprises computing a blood flow for the tissue.

Example 12 comprises the subject matter of any variation of any of example(s) 1-11, wherein computing one or more quantitative perfusion parameters for the tissue comprises computing a flow rate to fill an intravascular volume of the tissue.

Example 13 comprises the subject matter of any variation of any of example(s) 1-12, wherein computing one or more quantitative perfusion parameters for the tissue comprises computing one or more quantitative perfusion parameters for a plurality of super-voxels of the processed 4D perfusion image data, wherein each super-voxel of the processed 4D perfusion image data comprises a plurality of voxels of the processed 4D perfusion image data having similar temporal characteristics and spatial constraint.

Example 14 comprises the subject matter of any variation of any of example(s) 1-13, wherein the operations, when executed, further cause the processor to estimate one or more confidence intervals associated with the one or more quantitative perfusion parameters.

Example 15 comprises the subject matter of any variation of any of example(s) 1-14, wherein the one or more quantitative perfusion parameters for the tissue are computed based at least in part on a model incorporating physiological constraints associated with the tissue.

Example 16 is an apparatus that facilitates system-independent calculation of one or more quantitative perfusion parameters, the apparatus comprising: a processor; a memory configured to store 4D (Four Dimensional) perfusion imaging data of a tissue, where the 4D perfusion imaging data comprises a plurality of 3D (Three Dimensional) stacks of perfusion imaging data over time; an input/output (I/O) interface; a set of circuits; and an interface that connects the processor, the memory, the I/O interface, and the set of circuits, the set of circuits comprising: an image acquisition circuit configured to access the 4D perfusion imaging data of the tissue; at least one of one or more artifact reduction circuits or one or more post-processing circuits configured to perform at least one of artifact reduction or post-processing on the 4D perfusion image data to generate processed 4D perfusion image data; a perfusion computation circuit configured to compute the one or more quantitative perfusion parameters for the tissue based at least in part on the processed 4D perfusion image data; and a display circuit configured to output a visual representation of the one or more quantitative perfusion parameters.

Example 17 comprises the subject matter of any variation of any of example(s) 16, wherein the 4D perfusion imaging data comprises 4D CT (Computed Tomography) perfusion imaging data, and wherein the at least one of one or more artifact reduction circuits or one or more post-processing circuits is configured to perform Automated Beam Hardening Correction (ABHC) on the 4D perfusion imaging data to reduce beam hardening artifacts in the 4D perfusion imaging data.

Example 18 comprises the subject matter of any variation of any of example(s) 16-17, wherein the perfusion computation circuit is further configured to estimate one or more confidence intervals associated with the one or more quantitative perfusion measurements.

Example 19 is a method that facilitates system-independent calculation of one or more quantitative perfusion parameters, the method comprising: accessing 4D (Four Dimensional) perfusion imaging data of a tissue, where the 4D perfusion imaging data comprises a plurality of 3D (Three Dimensional) stacks of perfusion imaging data over time; performing at least one of artifact reduction or post-processing on the 4D perfusion image data to generate processed 4D perfusion image data; computing the one or more quantitative perfusion parameters for the tissue based at least in part on the processed 4D perfusion image data; and outputting a visual representation of the one or more quantitative perfusion parameters.

Example 20 comprises the subject matter of any variation of any of example(s) 19, wherein the one or more quantitative perfusion parameters comprises a blood flow in the tissue, and wherein the visual representation of the one or more quantitative perfusion parameters comprises a visual representation of the blood flow in the tissue.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    accessing 4D (Four Dimensional) perfusion imaging data of a tissue, where the 4D perfusion imaging data comprises a plurality of 3D (Three Dimensional) stacks of perfusion imaging data over time;
    performing at least one of artifact reduction or post-processing on the 4D perfusion image data to generate processed 4D perfusion image data;
    computing a quantitative perfusion map for the tissue from the processed 4D perfusion image data, wherein the quantitative perfusion map is computed based at least in part on a model that takes into account an effect on the tissue of physiological constraints associated with an interaction between intravascular and extravascular regions of the tissue, wherein computing the quantitative perfusion map for the tissue comprises computing a single Hounsfield unit over a plurality of voxels within a super-voxel of the processed 4D perfusion image data, wherein the plurality of voxels within the super-voxel of the processed 4D perfusion image data have similar temporal characteristics and spatial constraints; and
    outputting a visual representation of the quantitative perfusion map.

2. The non-transitory computer-readable medium of claim 1, wherein the 4D perfusion imaging data comprises one of 4D CT (Computed Tomography) perfusion imaging data, 4D MRI (Magnetic Resonance Imaging) perfusion imaging data, 4D ultrasound perfusion imaging data, 4D PET (Positron-Emission Tomography) perfusion imaging data, or 4D SPECT (Single-Photon Emission Computed Tomography) perfusion imaging data.

3. The non-transitory computer-readable medium of claim 2, wherein the quantitative perfusion map comprises both the intravascular and extravascular regions of the tissue.

4. The non-transitory computer-readable medium of claim 3, further comprising:
    performing Automated Beam Hardening Correction (ABHC) on the 4D perfusion imaging data by iteratively adjusting one or more ABHC correction parameters of an ABHC correction model to minimize an ABHC cost function, wherein the ABHC cost function comprises a first term that addresses bright and dark artifacts in a myocardium and a second term that addresses cupping artifacts.

5. The non-transitory computer-readable medium of claim 1, further comprising:
    constructing the quantitative perfusion map directly from the processed 4D perfusion image data.

6. The non-transitory computer-readable medium of claim 1, wherein performing at least one of artifact reduction or post-processing comprises:
    segmenting the 4D perfusion imaging data into highly attenuating materials data and water data;

forming a highly attenuating image from the highly attenuating materials data and a water image from the water data; and utilizing the highly attenuating image and the water image to modify the 4D perfusion image data.

7. The non-transitory computer-readable medium of claim 1, wherein performing at least one of artifact reduction or post-processing comprises correcting for partial scan acquisitions and reconstructions by determining an artifact correction that is a difference between an average of a full dynamic image sequence and an average of partial scan images.

8. The non-transitory computer-readable medium of claim 1, wherein performing at least one of artifact reduction or post-processing comprises reducing an effect of fluctuations from partial scan artifacts via applying a spatio-temporal filter to the 4D perfusion imaging data in two different steps, wherein the two different steps comprise performing a 3D non-linear diffusion filtration in a spatial domain and subsequently operating on adjacent temporal positions.

9. The non-transitory computer-readable medium of claim 1, wherein performing at least one of artifact reduction or post-processing comprises, for each 3D stack of the plurality of 3D stacks of perfusion imaging data, reformatting axial slices of that 3D stack into cardiac axis slices that span coverage of a heart.

10. The non-transitory computer-readable medium of claim 9, wherein performing at least one of artifact reduction or post-processing comprises segmenting the cardiac axis slices via applying smooth contours to the 4D perfusion imaging data based on a plurality of user-defined points.

11. The non-transitory computer-readable medium of claim 1, further comprising:
minimizing motion between image frames at edges between a myocardium blood pool and a ventricle blood pools or between a myocardium and a lung.

12. The non-transitory computer-readable medium of claim 1, further comprising:
registering image volumes at each time point to an image volume at peak left ventricle cavity enhancement.

13. The non-transitory computer-readable medium of claim 1, wherein the operations, when executed, further cause the processor to estimate one or more confidence intervals associated with the quantitative perfusion map, wherein the one or more confidence intervals are determined by:
calculating a joint confidence region;
determining a maximum blood flow and a minimum blood flow within the joint confidence region; and
determining a range between the maximum blood flow and the minimum blood flow.

14. A non-transitory computer-readable medium storing computer-executable instructions that, when executed, cause a processor to perform operations, comprising:
accessing 4D (Four Dimensional) perfusion imaging data of a tissue, where the 4D perfusion imaging data comprises a plurality of 3D (Three Dimensional) stacks of perfusion imaging data over time;
registering image volumes at each time point to an image volume at peak left ventricle cavity enhancement;
performing at least one of artifact reduction or post-processing on the 4D perfusion image data to generate processed 4D perfusion image data;
computing a quantitative perfusion map for the tissue from the processed 4D perfusion image data, wherein the quantitative perfusion map is computed based at least in part on a model that takes into account an effect on the tissue of physiological constraints associated with an interaction between intravascular and extravascular regions of the tissue; and
outputting a visual representation of the quantitative perfusion map.

15. The non-transitory computer-readable medium of claim 14, further comprising:
minimizing motion between image frames between a myocardium blood pool and a ventricle blood pools or between a myocardium and a lung.

16. The non-transitory computer-readable medium of claim 14,
wherein performing at least one of artifact reduction or post-processing comprises segmenting cardiac axis slices via applying smooth contours to the 4D perfusion imaging data based on a plurality of user-defined points.

17. A non-transitory computer-readable medium storing computer-executable instructions that, when executed, cause a processor to perform operations, comprising:
accessing 4D (Four Dimensional) perfusion imaging data of a tissue, where the 4D perfusion imaging data comprises a plurality of 3D (Three Dimensional) stacks of perfusion imaging data over time;
performing at least one of artifact reduction or post-processing on the 4D perfusion image data to generate processed 4D perfusion image data;
computing a quantitative perfusion map for the tissue from the processed 4D perfusion image data, wherein the quantitative perfusion map is computed based at least in part on a model that takes into account an effect on the tissue of physiological constraints associated with an interaction between intravascular and extravascular regions of the tissue;
outputting a visual representation of the quantitative perfusion map; and
estimating one or more confidence intervals associated with the quantitative perfusion map, wherein the one or more confidence intervals are determined by:
calculating a joint confidence region;
determining a maximum blood flow and a minimum blood flow within the joint confidence region; and
determining a range between the maximum blood flow and the minimum blood flow.

18. The non-transitory computer-readable medium of claim 17, wherein the quantitative perfusion map comprises an intravascular region of the tissue.

19. The non-transitory computer-readable medium of claim 17, wherein computing one or more quantitative perfusion maps for the tissue comprises computing a flow rate to fill an intravascular volume of the tissue.

20. The non-transitory computer-readable medium of claim 17, wherein performing at least one of artifact reduction or post-processing comprises performing Automated Beam Hardening Correction (ABHC) on the 4D perfusion imaging data to reduce beam hardening artifacts in the 4D perfusion imaging data.

* * * * *